(12) United States Patent  (10) Patent No.: US 8,545,513 B2
Blair et al.  (45) Date of Patent: Oct. 1, 2013

(54) UTERINE MANIPULATOR ASSEMBLIES AND RELATED COMPONENTS AND METHODS

(75) Inventors: Kerry Blair, Overland Park, KS (US);
Michael Long, Wayland, MA (US);
Robert Williams, Norwalk, CT (US);
Eric Sugalski, Arlington, MA (US);
Michael Susi, Marlborough, MA (US);
Tyson Lawrence, Cambridge, MA (US)

(73) Assignee: CooperSurgical, Inc., Trumbull, CT (US)

( * ) Notice: Subject to any disclaimer, the term of this patent is extended or adjusted under 35 U.S.C. 154(b) by 438 days.

(21) Appl. No.: 12/565,367

(22) Filed: Sep. 23, 2009

(65) Prior Publication Data

US 2010/0106163 A1  Apr. 29, 2010

Related U.S. Application Data

(60) Provisional application No. 61/108,211, filed on Oct. 24, 2008.

(51) Int. Cl.
*A61B 17/42* (2006.01)

(52) U.S. Cl.
USPC ............................................. 606/119

(58) Field of Classification Search
USPC ................. 606/119; 600/591, 204; 604/279; 128/832
See application file for complete search history.

(56) References Cited

U.S. PATENT DOCUMENTS

| | | | |
|---|---|---|---|
| 1,856,295 A | 5/1932 | Sovatkin |
| 2,186,143 A | 1/1940 | Neugass |
| 2,456,806 A | 12/1948 | Wolffe |
| 2,744,708 A | 5/1956 | Bedford, Jr. |
| 3,096,764 A | 7/1963 | Hiebert |
| 3,131,690 A | 5/1964 | Innis et al. |
| 3,153,267 A | 10/1964 | Rowland, Jr. |
| 3,196,865 A | 7/1965 | Rose |
| 3,749,088 A | 7/1973 | Kohlmann |
| 3,766,909 A | 10/1973 | Ozbey |
| 3,769,983 A | 11/1973 | Merav |
| 3,877,433 A | 4/1975 | Librach |

(Continued)

FOREIGN PATENT DOCUMENTS

| | | |
|---|---|---|
| DE | 20110921 | 12/2001 |
| DE | 69532474 | 11/2004 |

(Continued)

OTHER PUBLICATIONS

Culligan et al., "Long-Term Success of Abdominal Sacral Colpopexy Using Synthetic Mesh," Am. J. Obstet. Gynecol., Dec. 2002.

(Continued)

*Primary Examiner* — Ryan Severson
*Assistant Examiner* — Anh Dang
(74) *Attorney, Agent, or Firm* — Fish & Richardson P.C.

(57) ABSTRACT

A uterine manipulator includes an elongate shaft and a tip hub. The elongate shaft has a proximal end and a distal end. The distal end is configured to be inserted into a vagina. The tip hub is disposed at the distal end and is configured to releasably receive and support a tip mount for engaging a uterus. The elongate shaft includes one or more channels extending between the distal and proximal ends. The channels are configured to releasably receive catheter tubing.

32 Claims, 25 Drawing Sheets

(56) References Cited

U.S. PATENT DOCUMENTS

| | | | |
|---|---|---|---|
| 3,878,848 A | 4/1975 | Hiebert | |
| 3,948,270 A | 4/1976 | Hasson | |
| 4,022,208 A | 5/1977 | Valtchev | |
| 4,066,071 A | 1/1978 | Nagel | |
| 4,323,057 A | 4/1982 | Jamieson | |
| 4,430,076 A | 2/1984 | Harris | |
| 4,533,349 A | 8/1985 | Bark | |
| 4,562,832 A | 1/1986 | Wilder et al. | |
| 4,597,030 A | 6/1986 | Brody et al. | |
| 4,627,421 A | 12/1986 | Symbas et al. | |
| 4,775,362 A * | 10/1988 | Kronner | 604/103.05 |
| 4,807,625 A | 2/1989 | Singleton | |
| 4,823,167 A | 4/1989 | Manska et al. | |
| 4,981,355 A | 1/1991 | Higgins | |
| 4,996,974 A | 3/1991 | Ciarlei | |
| 4,997,419 A | 3/1991 | Lakatos et al. | |
| 5,059,198 A | 10/1991 | Gimpelson | |
| 5,104,377 A | 4/1992 | Levine | |
| 5,174,276 A | 12/1992 | Crockard | |
| 5,181,842 A | 1/1993 | Sunderland et al. | |
| 5,209,754 A | 5/1993 | Ahluwalia | |
| 5,232,443 A | 8/1993 | Leach | |
| 5,237,985 A | 8/1993 | Hodgson et al. | |
| 5,242,240 A | 9/1993 | Gorham | |
| 5,259,836 A | 11/1993 | Thurmond et al. | |
| 5,273,026 A | 12/1993 | Wilk | |
| 5,338,297 A * | 8/1994 | Kocur et al. | 604/103.03 |
| 5,409,496 A | 4/1995 | Rowden et al. | |
| 5,431,662 A | 7/1995 | Nicholas | |
| 5,520,698 A | 5/1996 | Koh | |
| 5,540,700 A * | 7/1996 | Rowden et al. | 606/119 |
| 5,549,563 A | 8/1996 | Kronner | |
| 5,571,115 A | 11/1996 | Nicholas | |
| 5,624,399 A | 4/1997 | Ackerman | |
| 5,643,285 A | 7/1997 | Rowden et al. | |
| 5,690,617 A | 11/1997 | Wright | |
| 5,810,806 A | 9/1998 | Ritchart et al. | |
| 5,835,657 A | 11/1998 | Suarez et al. | |
| 5,840,077 A * | 11/1998 | Rowden et al. | 606/119 |
| 6,068,121 A | 5/2000 | McGlinch | |
| 6,080,118 A | 6/2000 | Blythe | |
| 6,159,170 A | 12/2000 | Borodulin et al. | |
| 6,328,729 B1 | 12/2001 | Jervis | |
| 6,348,036 B1 | 2/2002 | Looney et al. | |
| 6,423,075 B1 | 7/2002 | Singh et al. | |
| 6,651,992 B1 | 11/2003 | Smith | |
| 6,682,100 B2 | 1/2004 | Wood et al. | |
| 6,741,895 B1 | 5/2004 | Gafni et al. | |
| 6,752,819 B1 | 6/2004 | Brady et al. | |
| 6,932,759 B2 | 8/2005 | Kammerer et al. | |
| 7,052,453 B2 | 5/2006 | Presthus et al. | |
| 7,334,503 B1 | 2/2008 | Newman | |
| 2001/0021854 A1 | 9/2001 | Donnez et al. | |
| 2003/0187334 A1 | 10/2003 | Biswas | |
| 2003/0195386 A1 | 10/2003 | Thierfeld et al. | |
| 2003/0220538 A1 | 11/2003 | Jacquetin | |
| 2004/0138528 A1 | 7/2004 | Richter et al. | |
| 2004/0193043 A1 * | 9/2004 | Duchon et al. | 600/431 |
| 2004/0230092 A1 | 11/2004 | Thierfeld et al. | |
| 2005/0065395 A1 | 3/2005 | Mellier | |
| 2005/0085827 A1 | 4/2005 | G. et al. | |
| 2005/0277948 A1 | 12/2005 | Cedars | |
| 2006/0015001 A1 | 1/2006 | Staskin et al. | |
| 2006/0199994 A1 | 9/2006 | Inman et al. | |
| 2006/0241652 A1 | 10/2006 | Doll et al. | |
| 2007/0088351 A1 | 4/2007 | Ewaschuk et al. | |
| 2007/0129615 A1 | 6/2007 | Backman et al. | |
| 2008/0221590 A1 | 9/2008 | Ikeda et al. | |
| 2008/0243176 A1 * | 10/2008 | Weitzner et al. | 606/206 |
| 2009/0131954 A1 | 5/2009 | Christian et al. | |
| 2010/0106163 A1 | 4/2010 | Blair et al. | |
| 2010/0152749 A1 | 6/2010 | Von Pechmann et al. | |
| 2010/0168784 A1 | 7/2010 | Pustilnik | |
| 2010/0179575 A1 | 7/2010 | Von Pechmann et al. | |
| 2010/0280309 A1 | 11/2010 | Von Pechmann | |
| 2011/0130769 A1 | 6/2011 | Boebel et al. | |

FOREIGN PATENT DOCUMENTS

| | | |
|---|---|---|
| DE | 10341561 | 4/2005 |
| EP | 0400458 | 12/1990 |
| EP | 0890342 | 1/1999 |
| WO | WO 2008/074054 | 6/2008 |
| WO | WO 2009/078953 | 6/2009 |

OTHER PUBLICATIONS

"KOH Cup Vaginal Fornices Delineator & Colpo-Pneumo Occluder," *The Koh Colpotomizer © System*, Directions for Use; 6 pages; Sep. 2008.

"Laparoscopic Hysterectomy and Colpotomy Accessories for Use Exclusively with the RUMI System Uterine Manipulator," *CooperSurgical The KOH Colpotomizer System*; 2 pages; Oct. 2006.

* cited by examiner

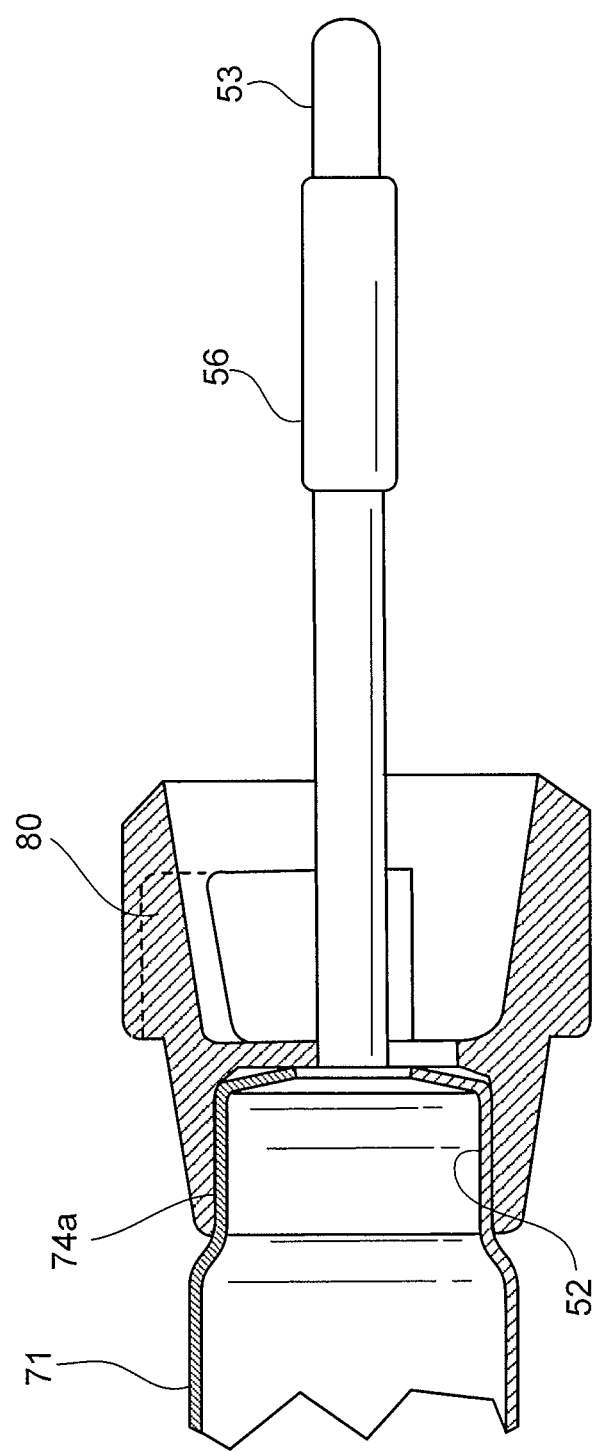

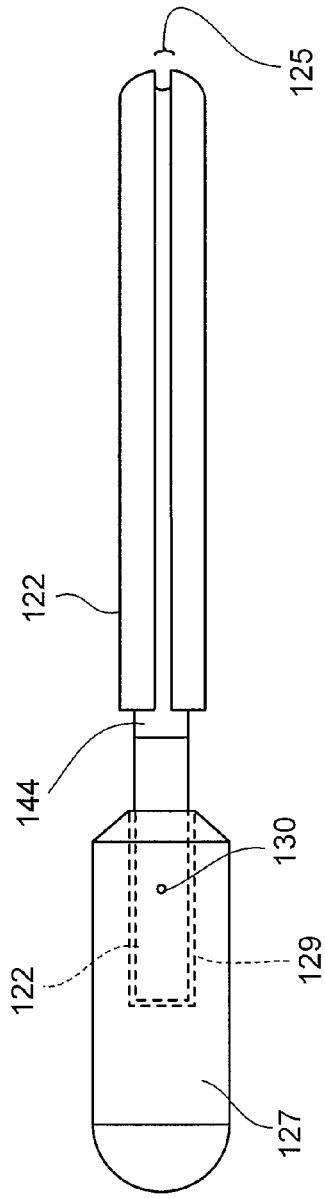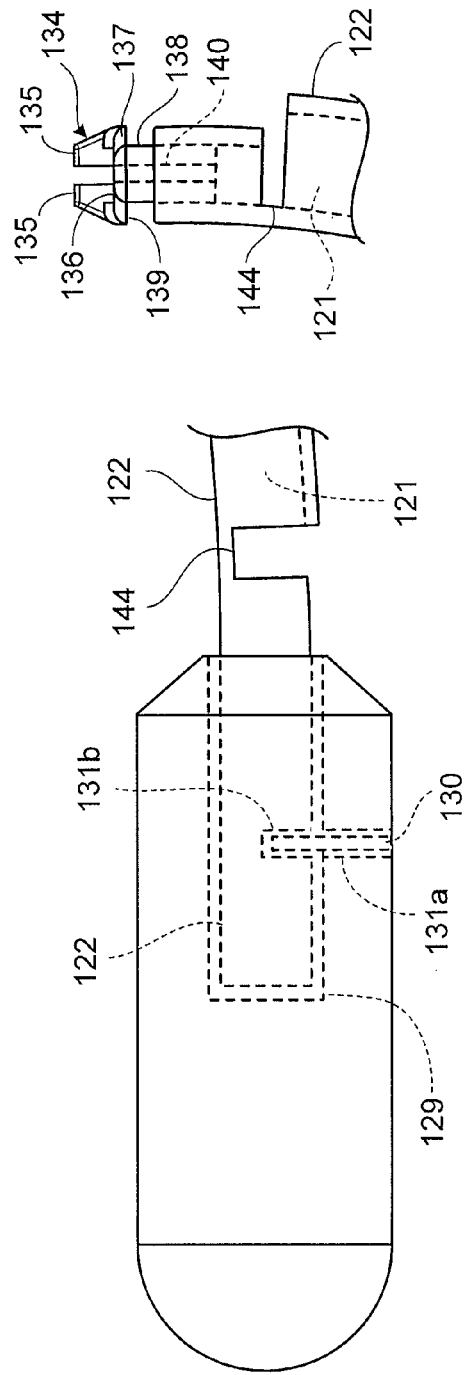

UTERINE MANIPULATOR ASSEMBLIES AND RELATED COMPONENTS AND METHODS

CROSS-REFERENCE TO RELATED APPLICATIONS

This application claims the benefit under 35 U.S.C. §119 (e) of U.S. Application Ser. No. 61/108,211, filed on Oct. 24, 2008, which is incorporated by reference herein.

TECHNICAL FIELD

This disclosure relates to uterine manipulator assemblies and related components and methods.

BACKGROUND

Uterine manipulator assemblies are medical instruments that are used for manipulating (e.g., moving or repositioning) a patient's uterus during medical procedures. Such procedures include surgical procedures such as laparoscopic gynecologic surgery, e.g., total laparoscopic hysterectomy (TLH) surgery, and diagnostic procedures such as chromopertubation in which a colored dye is delivered to a patient's fallopian tubes to confirm that they are patent.

Instruments of this kind often include a proximal portion that remains external to the patient's body during use and a distal portion that is inserted into the patient's body. The proximal portion typically provides for manipulation of the instrument during use. The distal portion often includes a tip that is sized to be inserted into and/or engage a uterus and which, in some cases, is configured for delivering liquid (e.g., dye) to a patient's uterus and/or fallopian tubes. Generally, the distal portion of the instrument is advanced through the vaginal cavity and into the uterus. With the distal portion inserted within a uterus, the uterus can be manipulated through surgeon or physician controlled movements of the proximal portion. Following completion of a procedure, the instrument is removed from the patient's body via the vaginal cavity.

SUMMARY

In general, this disclosure relates to uterine manipulation assemblies and related components and methods. The uterine manipulation assemblies can be used, for example, for manipulating a patient's uterus during gynecological surgery and/or gynecological diagnostic procedures.

In one aspect, a uterine manipulator includes an elongate shaft and a tip hub. The elongate shaft has a proximal end and a distal end. The distal end is configured to be inserted into a vagina. The tip hub is disposed at the distal end and is configured to releasably receive and support a tip mount for engaging a uterus. The elongate shaft includes one or more channels extending between the distal and proximal ends. The channels are configured to releasably receive catheter tubing.

In another aspect, a uterine manipulator assembly includes a tip mount and a uterine manipulator. The tip mount includes a tip configured to extend into a uterus and one or more catheter tubes in fluid communication with the tip. The uterine manipulator includes an elongate shaft and a tip hub. The elongate shaft has a proximal end and a distal end. The distal end is configured to be inserted into a vagina. The tip hub is disposed at the distal end and is configured to releasably receive and support the tip mount. The elongate shaft includes one or more channels extending between the distal and proximal ends and configured to releasably receive the one or more catheter tubes of the tip mount.

In a further aspect, a method includes mounting a tip mount to a uterine manipulator and then inserting one or more catheter tubes of the tip mount into one or more channels in the uterine manipulator.

In yet another aspect, a uterine manipulator assembly includes a uterine manipulator and a cup. The uterine manipulator includes an elongate shaft having a proximal end and a distal end, the distal end being configured to be inserted into a vagina. The cup includes a first open end configured to receive a cervix. The cup is configured to be coupled to the uterine manipulator such that the cup is slidable between the proximal and distal ends of the elongate shaft.

According to another aspect, a uterine manipulating tip assembly includes a tip mount, a cup, and one or more collapsible connecting members connecting the cup and the tip mount. The tip mount is configured to be secured to a uterine manipulator. The tip mount includes a tip configured to extend into a uterus. The cup includes a first open end configured to receive a cervix.

Embodiments of the disclosed methods, systems and devices may include one or more of the following features.

In some embodiments, the elongate shaft is substantially arcuate.

The tip hub can be configured to align a received tip mount in a predetermined position relative to the one or more channels of the elongate shaft.

The elongate shaft can include a mounting interface.

The mounting interface can include one or more flat regions on the elongate shaft.

The uterine manipulator can include a handle disposed at the proximal end of the elongate shaft.

The elongate shaft can include multiple channels. The multiple channels can be spaced radially about the elongate shaft.

In some cases, each of the one or more channels is configured to receive and support a single catheter tube.

In some embodiments, each of the one or more channels is configured to retain the catheter tubes in a position substantially flush with an outer surface of the elongate shaft.

The elongate shaft can also include one or more openings extending along the channels and configured to allow catheter tubing to be inserted into and removed from the channels.

The elongate shaft can be formed of a material or materials capable of withstanding medical device sterilization procedures.

The uterine manipulator assembly can also include a cup configured to be coupled to the uterine manipulator. The cup can include a first open end configured to receive a cervix.

In some cases, the cup is configured to be coupled to the elongate shaft via the tip mount.

In some embodiments, the cup is configured to be coupled to the uterine manipulator such that the cup is slidable between the proximal and distal ends of the elongate shaft.

The uterine manipulator assembly can also include a vaginal occluder attached to the cup. The vaginal occluder being operable to inhibit the passage of fluid through a vaginal cavity.

In some cases, the cup is connected to the tip mount by one or more collapsible connecting members.

In some embodiments, the tip includes an expandable member and at least one of the one or more catheter tubes is in fluid communication with the expandable member.

The uterine manipulator assembly can also include a vaginal occluder configured to be coupled to the uterine manipulator. The vaginal occluder is operable to inhibit the passage of fluid through a vaginal cavity.

The vaginal occluder can be configured to be coupled to the uterine manipulator via the tip mount.

In some embodiments, the tip hub is configured to align the one or more catheter tubes of the tip mount in a predetermined position relative to the elongate shaft such that the one or more catheter tubes of the tip mount are substantially aligned with the one more channels.

In some examples, the uterine manipulator is reusable, and the tip mount is disposable and adapted for one-time use.

Methods can also include inserting the tip mount and the uterine manipulator into a vaginal cavity.

Methods can also include removing the uterine manipulator and the tip mount from the vaginal cavity; removing the one or more tubes from the one or more channels; and removing the tip mount from the uterine manipulator.

In some cases, methods can include discarding the tip mount; and sterilizing the uterine manipulator. Sterilizing the uterine manipulator can include heating the uterine manipulator in an autoclave.

Methods can also include reusing the uterine manipulator. Reusing the uterine manipulator can include mounting a second tip mount to the uterine manipulator and then inserting one or more catheter tubes of the second tip mount into the one or more channels in the uterine manipulator.

Methods can also include sliding a cup along the uterine manipulator between a proximal end of the uterine manipulator and the tip mount. The cup can include a first open end configured to receive a cervix.

The uterine manipulator assemblies can include a tip mount including a tip configured to extend into a uterus. The tip mount can be secured to the distal end of the elongate shaft.

In some cases, the cup is configured to mate with the tip mount.

In some embodiments, the cup is connected to the tip mount by one or more collapsible connecting members.

The uterine manipulator assemblies can also include a vaginal occluder attached to the cup. The vaginal occluder is operable to inhibit the passage of fluid through a vaginal cavity.

Embodiments can include one or more of the following advantages.

In some embodiments, the one or more channels function to hold catheter tubes and, thus, can help to inhibit the catheter tubes from interfering with other instrumentation during use (e.g., during surgery) and can also help to inhibit the catheter tubes from obstructing an operator's view during use.

In some cases, retaining catheter tubes within a channel or channels in or on a uterine manipulator can allow other devices, such as other medical instrumentation, to be advanced, e.g., coaxially, around or along the uterine manipulator, e.g., from a proximal end portion toward a distal end portion without interference with the catheter tubes.

Retaining catheter tubes within a channel or channels in or on a uterine manipulator can also help to inhibit tangling of the catheter tubes with each other and with other instrumentation, and can provide for better organization of the catheter tubes, such as when multiple catheter tubes are present and each has a different function.

Providing a channel or channels in or on a uterine manipulator that allow catheter tubes (e.g., of a tip mount) to be releaseably received can allow for easy removal of tip mounts from the uterine manipulator. This may be particularly beneficial where the uterine manipulator is reusable and the tip mounts are configured to be discarded after a single use.

Other aspects, features, and advantages are in the description, drawings, and claims.

DESCRIPTION OF DRAWINGS

FIG. 6 is a detailed, sectional view of a distal end portion of a uterine manipulator assembly.

FIG. 10C is a bottom view of the uterine manipulator of FIG. 10A.

FIG. 10D is a detailed view of a handle of the uterine manipulator of FIG. 10A.

FIG. 10E is a detailed view of a tip hub of the uttering manipulator of FIG. 10A.

DETAILED DESCRIPTION

Figure 1A:
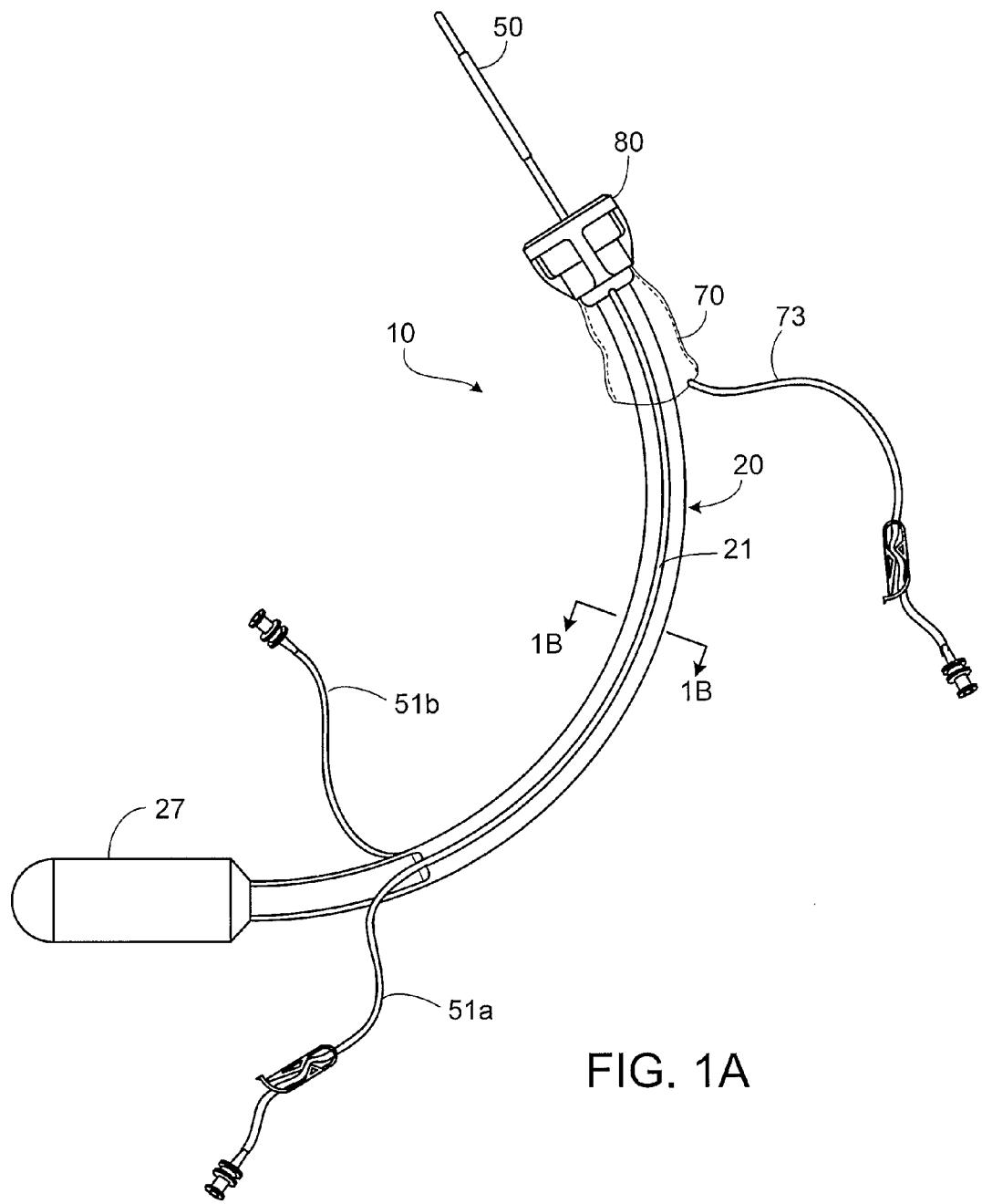
FIG. 1A is a side view of a uterine manipulator assembly.
Figure 1B:
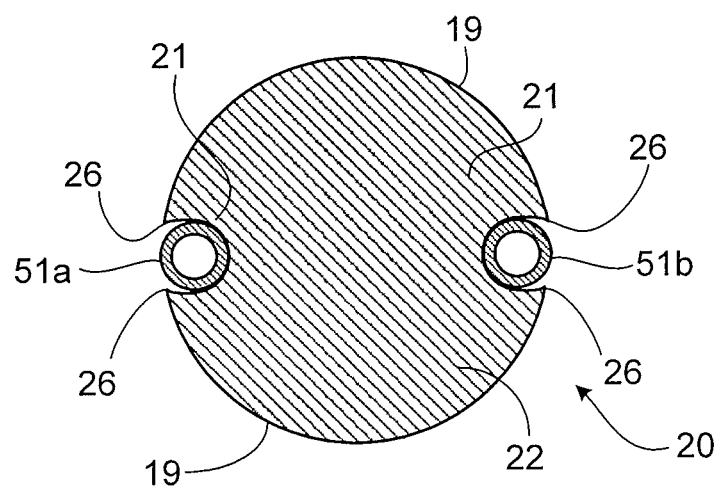
FIG. 1B is a cross-sectional view of the uterine manipulator assembly of FIG. 1A, taken along line 1B-1B.
Figure 2:
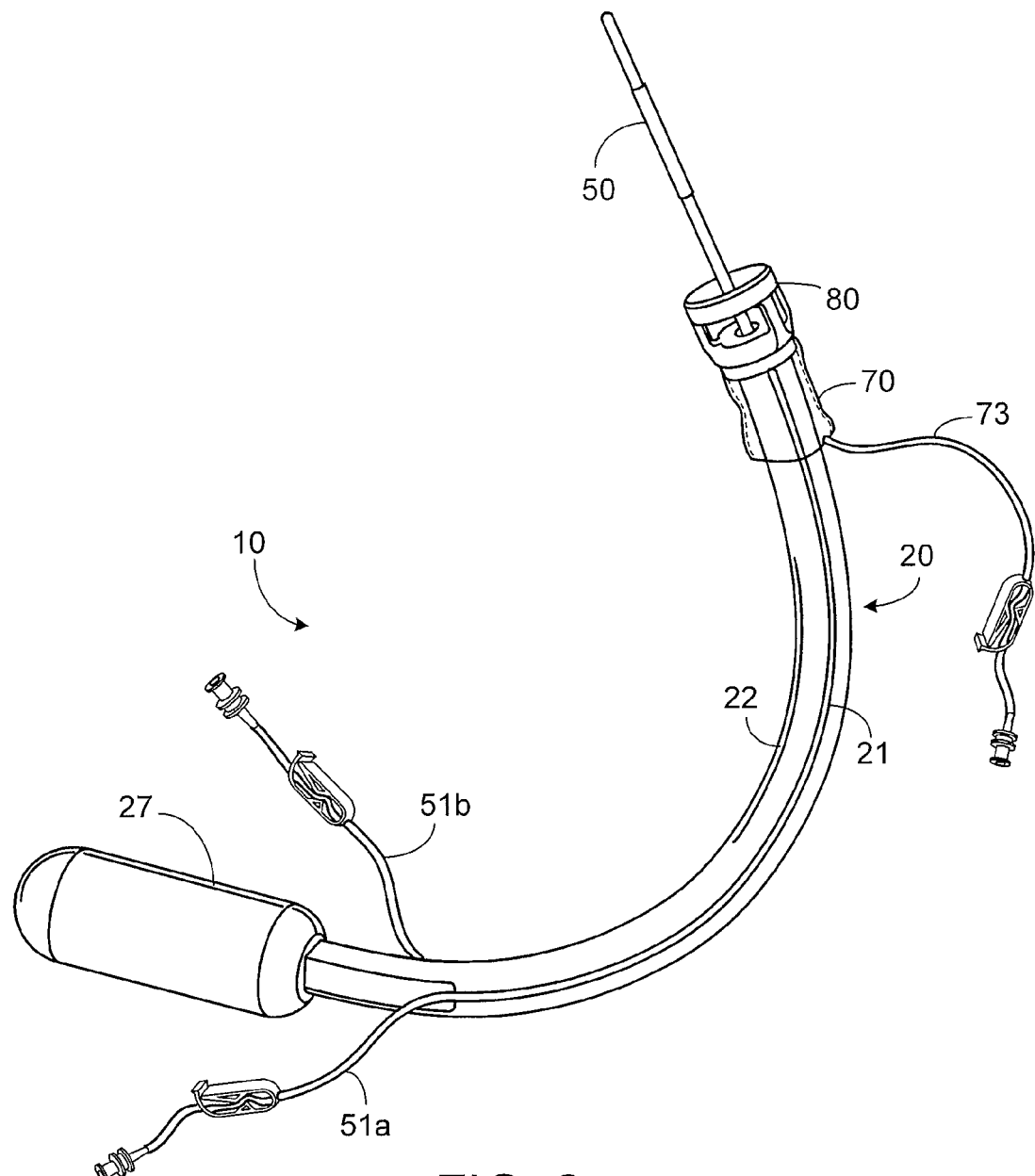
FIG. 2 is a perspective view of the uterine manipulator assembly of FIG. 1A.

FIGS. 1A, 1B and 2 illustrate a uterine manipulator assembly 10 adapted for insertion into a vaginal cavity for use in female pelvic surgical procedures. The uterine manipulator assembly 10 includes a uterine manipulator 20, a tip mount 50 releasably coupled to uterine manipulator 20, a vaginal occluder 70 releasably coupled to the tip mount 50, and a cervical cup 80. The uterine manipulator 20 is provided with channels 21 for releasably receiving and retaining catheter tubing 51 of the tip mount 50. The channels 21 can help to inhibit the catheter tubing 51 of the tip mount 50 from interfering with other instrumentation during use and can also help to inhibit the catheter tubing (i.e., catheter tubes 51a, 51b) from obstructing an operator's view during use, e.g., to provide a clear view of the cervix as the uterine manipulator assembly 10 is placed into position prior to or during surgery.

Figure 3A:
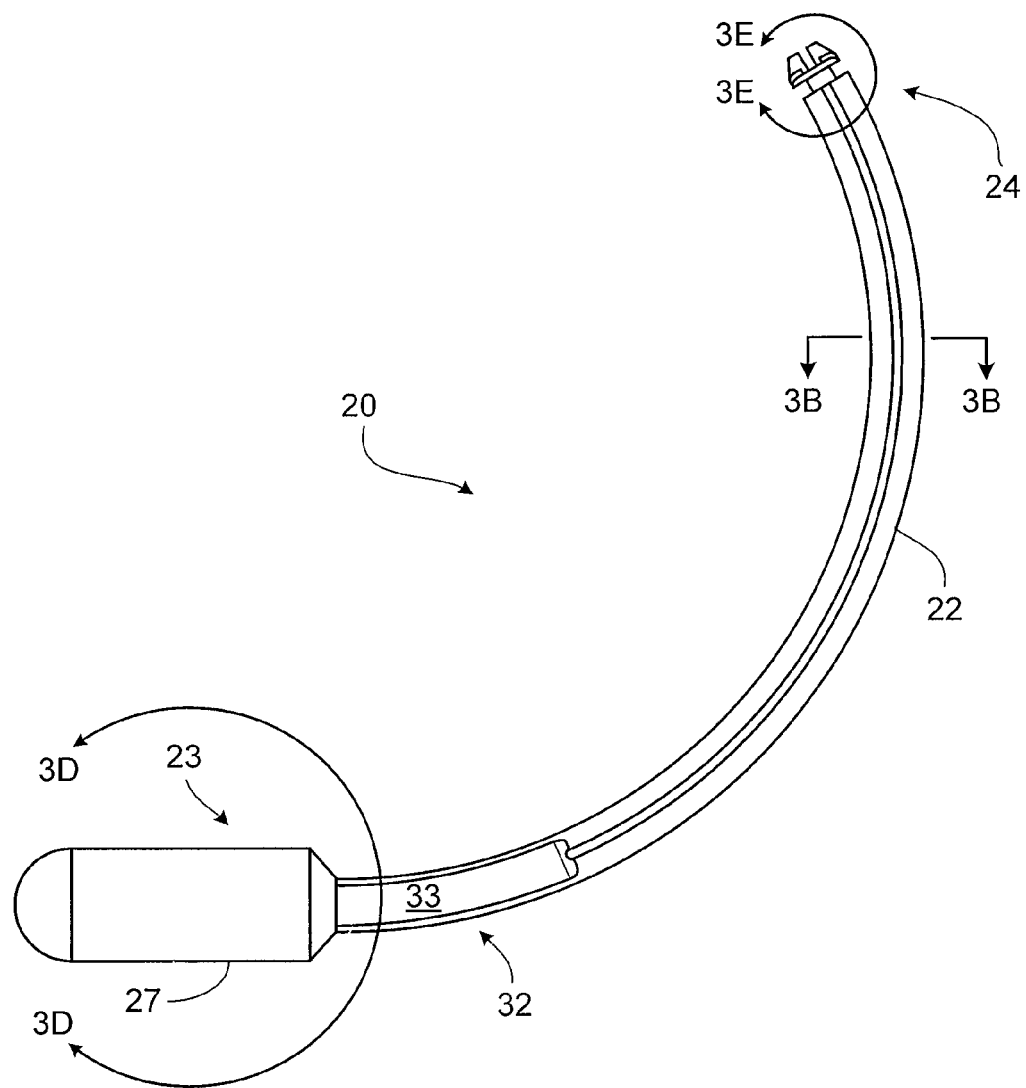
FIG. 3A is a side view of a uterine manipulator having radially spaced channels for receiving and retaining catheter tubes.
Figure 3B:
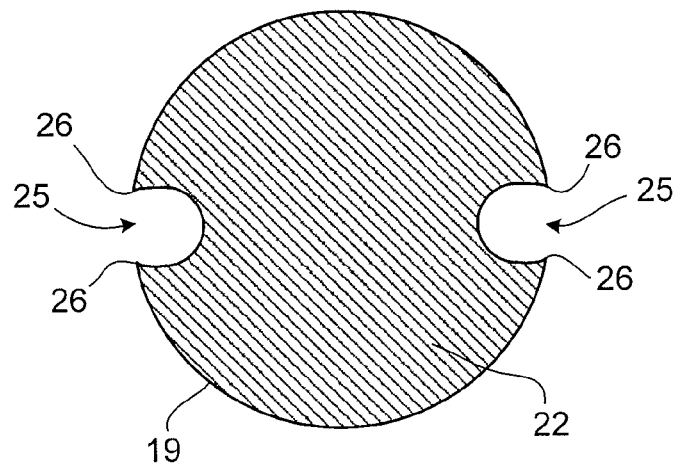
FIG. 3B is a cross-sectional view of the uterine manipulator of FIG. 3A, taken along line 3B-3B.

Referring to FIGS. 3A and 3B, the uterine manipulator 20 includes an elongate, arcuate shaft 22 having a proximal end portion 23 and a distal end portion 24. Referring to FIG. 3A, the channels 21 extend along an outer surface 19 of the shaft 22 between the distal end portion 24 and the proximal end portion 23. As shown in FIG. 3B, the channels 21 are spaced radially about the shaft 22, which is otherwise solid. The shaft 22 also includes openings 25 which extend along the length of the channels 21 and are substantially parallel thereto. The openings 25 allow the catheter tubes 51a, 51b (FIG. 1B) to be inserted into and removed from the channels 21. The openings 25 can be sized to be smaller than the channels 21 so as to provide the shaft 22 with overhangs 26 which help to retain the catheter tubing 51 within the channels 21 after insertion. In this regard, the channels 21 can be formed as undercuts with a ball tip mill. The channels 21 can have sufficient depth such that the catheter tubes 51a, 51b lie flush with, or are slightly recessed from, the outer surface 19 of the shaft 22 (as shown in FIG. 1B). This can allow devices, such as other medical instrumentation, to be advanced, e.g., coaxially, along the shaft 22 from the proximal end portion 23 toward the distal end portion 24 without interference with the catheter tubes 51a, 51b.

Figure 3C:
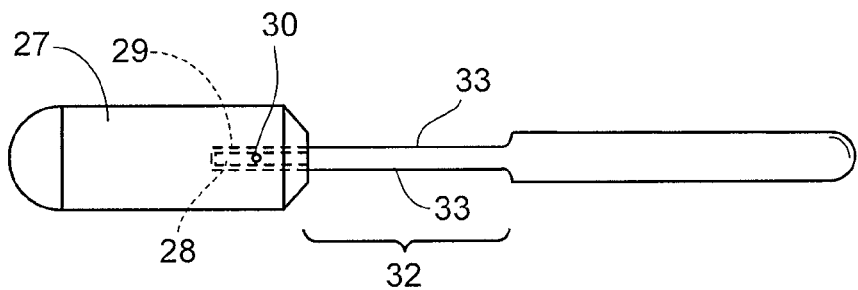
FIG. 3C is a bottom view of the uterine manipulator of FIG. 3A.
Figure 3D:
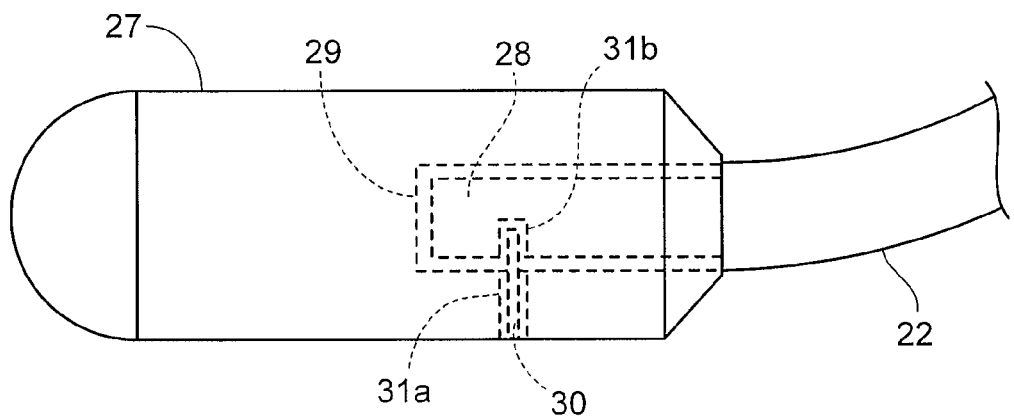
FIG. 3D is a detailed view of a handle of the uterine manipulator of FIG. 3A.

A handle 27 is coupled to the proximal end portion 23 of the arcuate shaft 22. The handle 27 can be integrally formed with shaft 22 or a separate piece. As shown, for example, in FIGS. 3C and 3D, the handle 27 that is mounted on a protrusion 28 of the shaft 22. In this regard, the handle 27 includes an aperture 29 which receives the protrusion 28. The handle 27 is slid over the shaft 22 such that the protrusion 28 extends into the aperture 29. Referring still to FIGS. 3C and 3D, the handle 27 is held in place, relative to shaft 22, by a set-pin 30 which includes a press-fit connection with a first through-hole 31a in the handle 27 and second through-hole 31b in the shaft 22. Alternatively or additionally, the handle 27 can be fixed to the shaft 22 with adhesive and/or threaded fastener(s) and/or the aperture 29 can be sized to provide a press-fit connection with the shaft 22.

Figure 3E:
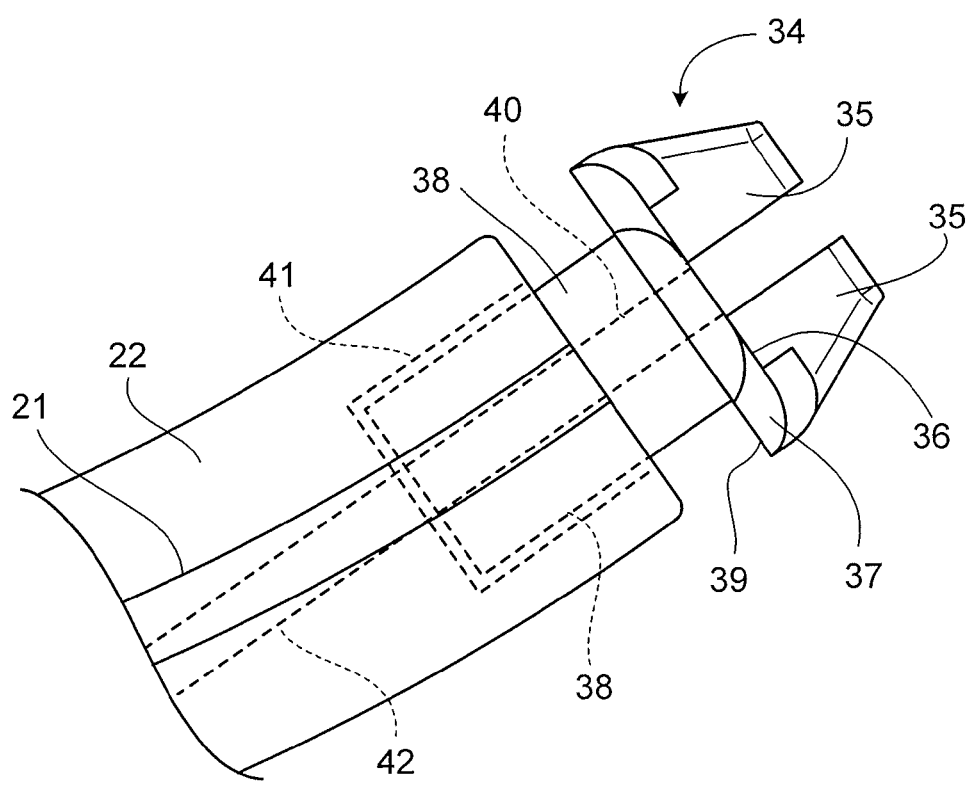
FIG. 3E is a detailed view of a tip hub of the uterine manipulator of FIG. 3A.

Adjacent the handle 22 is a mounting interface 32. As show in FIG. 3C, the mounting interface 32 includes a pair of diametrically opposed flat regions 33 formed on the shaft 22. The mounting interface 32 is configured to allow the shaft 22 to be mounted to an adapter of an apparatus for positioning and holding in place a manually manipulated medical device during the performance of a robotically assisted medical procedure, such as described in U.S. patent application Ser. No. 11/847,154, filed Aug. 29, 2007, the complete disclosure of which is incorporated herein by reference. Referring to FIG. 3E, the uterine manipulator 20 also includes a tip hub 34 disposed at the distal end portion 24. The tip hub 34 is configured to releasably receive and support the tip mount 50 (FIG. 1). The tip hub 34 includes a pair of spaced apart flats 35 which extend upwardly from a first surface 36 of a base 37. A stem 38 extends from a second surface 39, opposite the first surface 36 of the base 37. A through hole 40 extends from the first surface 36 of the base 37 through the stem 38 and is sized to receive a rod 61 (FIG. 4A) of the tip mount 50. The stem 38 is received in an aperture 41 in the shaft 22 in a press-fit manner, thereby securing the tip hub 34 to the shaft 22.

The various components of the uterine manipulator 20, including the shaft 22, the handle 27 and the tip hub 34 can be formed, e.g., molded and/or machined, from materials that are biocompatible and capable of withstanding medical device sterilization procedures, such as by heat-based methods (e.g., autoclave, steam autoclave, or dry heat oven) so that the uterine manipulator 20 as a whole is reusable. Suitable materials that are capable of withstanding medical device sterilization procedures include metals, such as stainless steel and aluminum, and polymers, such as Polyoxymethylene (POM) commonly known under the DuPont™ brand name Delrin®.

Figure 4A:
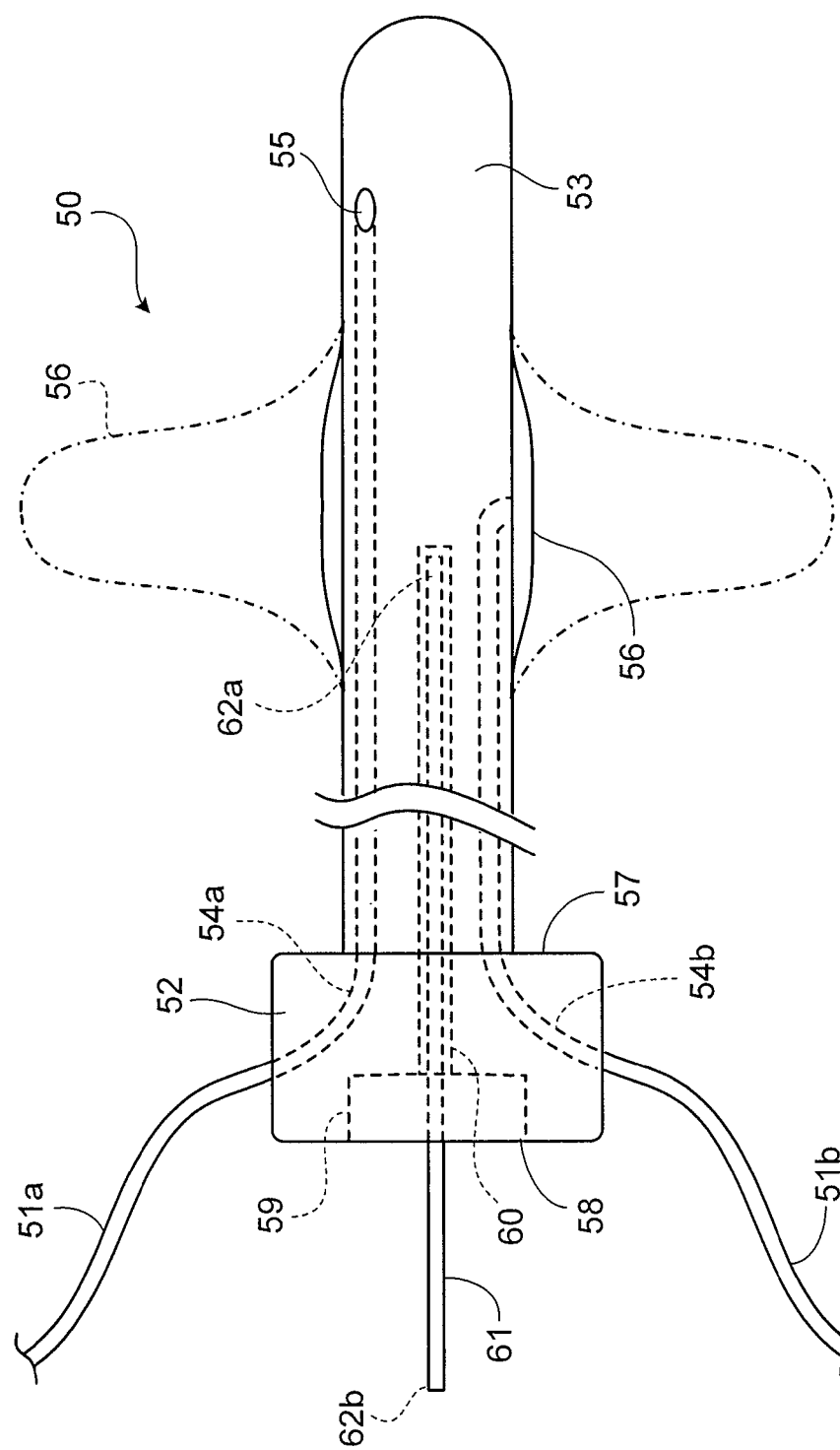
FIG. 4A is a side view of a tip mount for a uterine manipulator assembly.
Figure 4B:
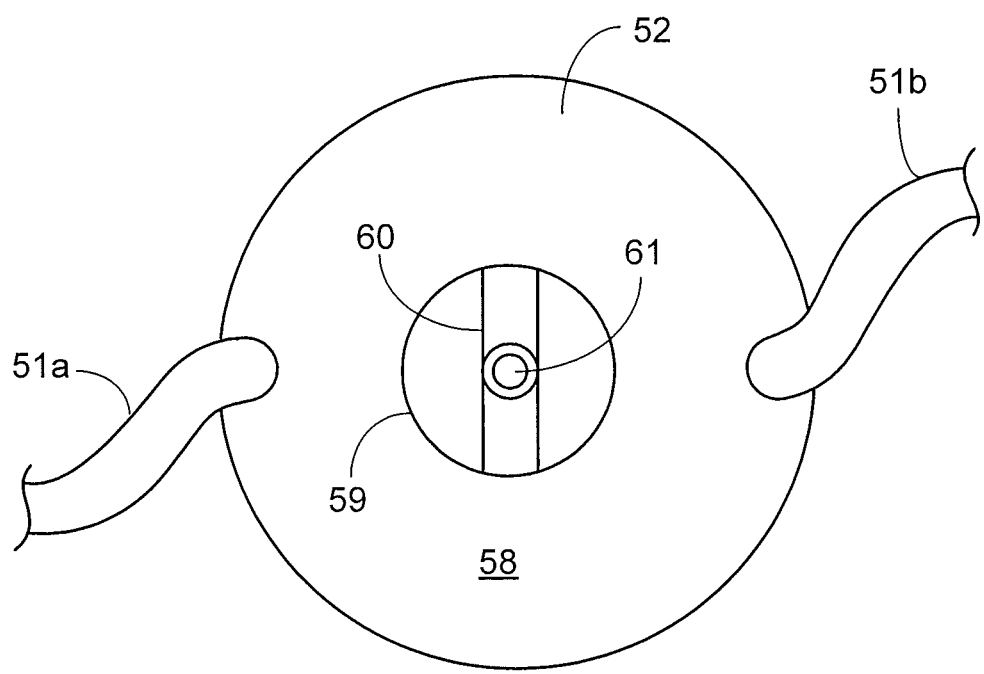
FIG. 4B is front view of the tip mount of FIG. 4A.

Referring to FIGS. 4A and 4B, the tip mount 50 includes a uterine manipulating tip base 52 and a uterine manipulating tip 53 that is configured to be inserted into a uterus. The catheter tubes 51a, 51b are connected to the uterine manipulating tip base 52 and include a dye catheter tube 51a, e.g., for delivering a liquid based dye to the uterine manipulating tip base 52, e.g., for chromopertubation procedures, and a balloon catheter tube 51b. The tip mount 50 includes a dye conduit 54a that provides for fluid communication between the dye catheter tube 51a and a tip bore 55 which extends through the uterine manipulating tip 53. The tip mount 50 also includes a balloon conduit 54b that provides for fluid communication between the balloon catheter tube 51b and an expandable balloon 56 surrounding the uterine manipulating tip 53. As shown in FIG. 4A, the uterine manipulating tip 53 extends from a first surface 57 of the uterine manipulating tip base 52. At a second surface 58, opposite the first surface 57, the uterine manipulating tip base 52 defines a counter-bore hole 59 which leads to a rectangular aperture 60. The tip hub 34 (FIG. 3E) is inserted into the counter-bore hole 59 into a position in which the spaced apart flats 35 engage the rectangular aperture 60 to force the tip mount 50 into a position, relative to the shaft 22, in which the catheter tubes 51a, 51b are substantially aligned with the channels 21. The tip mount 50 also includes the rod 61, e.g., metal rod, which includes a distal portion 62a that is disposed within the uterine manipulating tip 53, and a proximal portion 62b that extends outwardly from the second surface 58 of the uterine manipulating tip base 52. The proximal portion 62b of the rod 61 is inserted into the through hole 40 of the tip hub 34 during assembly and extends into a corresponding through hole 42 (FIG. 3E) in the shaft 22. The tip mount 50 including the uterine manipulating tip base 52, the uterine manipulating tip 53, and the catheter tubes 51a, 51b can be formed by molding, e.g., extruding, blow molding or injection molding) and can be formed of one or more medical grade materials. Medical grade plastics and/or rubber, e.g., natural or synthetic rubber (e.g., silicone compounds) can be used because of their ease of manufacturing, ready availability and disposable nature. Suitable tip mounts are commercially available from Cooper Surgical, Trumbull, Conn., under the RUMI® tips mark, such as Cooper Surgical item numbers UMW676, UMB678, UMG670, and UML516.

Figure 5:
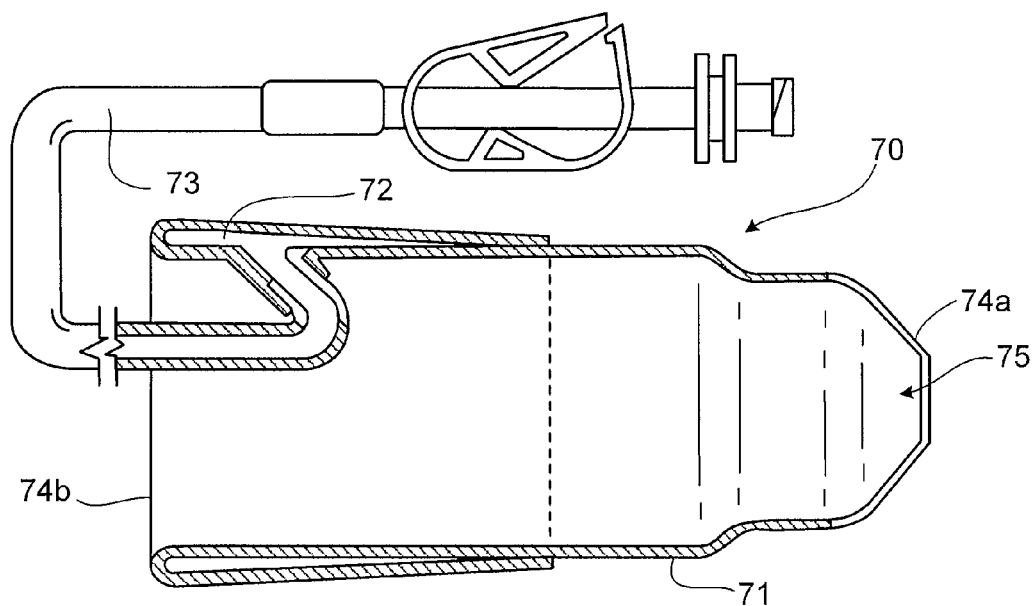
FIG. 5 is a side, cross-sectional view of a vaginal occluder.

Referring to FIG. 5, the vaginal occluder 70 includes a main body 71 including expandable balloon cuff 72, a balloon cuff catheter tube 73, and main body distal and proximal ends 74a, 74b. The balloon cuff catheter tube 74 is affixed to the balloon cuff 72 and communicates fluid to the balloon cuff 72 when inflation is desired. The vaginal occluder 70 may be constructed of a medical grade silicone suitable for injection molding. The distal end 74a includes an opening 75 having a diameter larger than the uterine manipulating tip 53 (FIG. 4A) and smaller than that of the uterine manipulating tip base 52. In particular, as illustrated in FIG. 6, the opening 75 is sized relative to the diameter of the uterine manipulating tip 53 and the uterine manipulating tip base 52 to permit the vaginal occluder 70 to be slidably received on the shaft 22 by pulling the proximal end 74b over the uterine manipulating tip 53 and the uterine manipulating tip base 52, such that the balloon cuff 72 is disposed in circumscribing relationship to the shaft 22. Further, as illustrated in FIG. 2, the vaginal occluder 70 is positioned on the shaft 22 so that the distal end 74a abuts against the first surface 57 of the uterine manipulating tip base 52. The cervical cup 80 may now be mounted on the uterine manipulating tip base 52 with the distal end 74a of the vaginal occluder 70 sandwiched therebetween. Once the vaginal occluder 70 is installed on the shaft 22 in the above described fashion and the distal end 74a is sandwich between uterine manipulating tip base 52 and the cervical cup 80, a seal is formed therein to prevent the flow of fluid (including gases) between the cervical cup 80 and the uterine manipulating tip base 52 during surgical procedures. The sandwich-like engagement of the distal end 74a between the base 52 and the cervical cup 80 also anchors the distal end 74a to the base 52 when the proximal end 74b of the vaginal occluder 70 is caused to be stretched in a direction opposite the distal end 74a. Suitable vaginal occluders are commercially available from Cooper Surgical, Trumbull, Conn., under the Colpo-Pneumo Occluder™ mark, such as Cooper Surgical item number CPO-6.

Figure 7A:
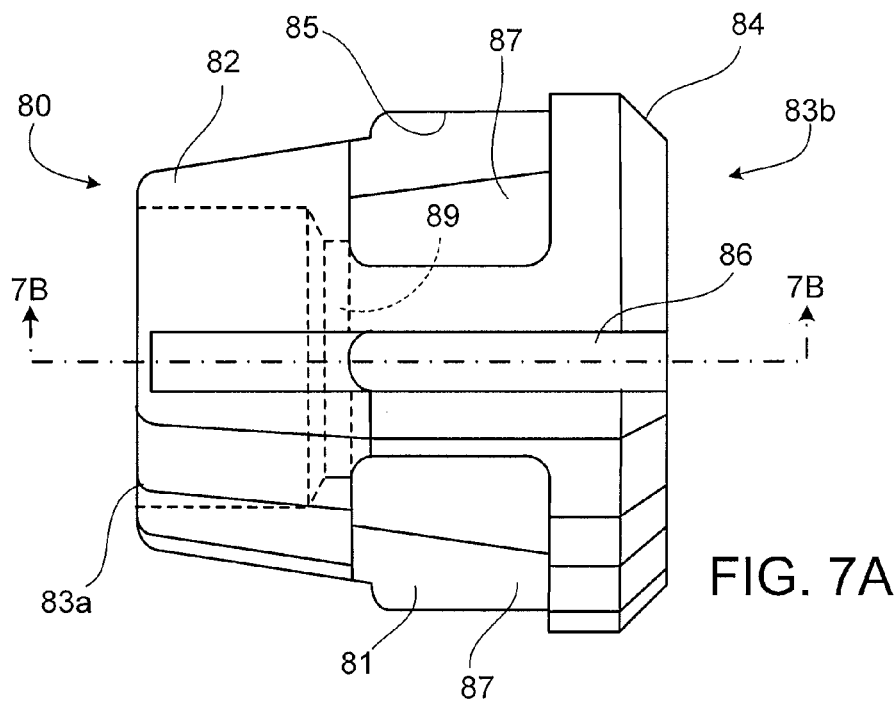
FIG. 7A is a side view of a cervical cup.
Figure 7B:
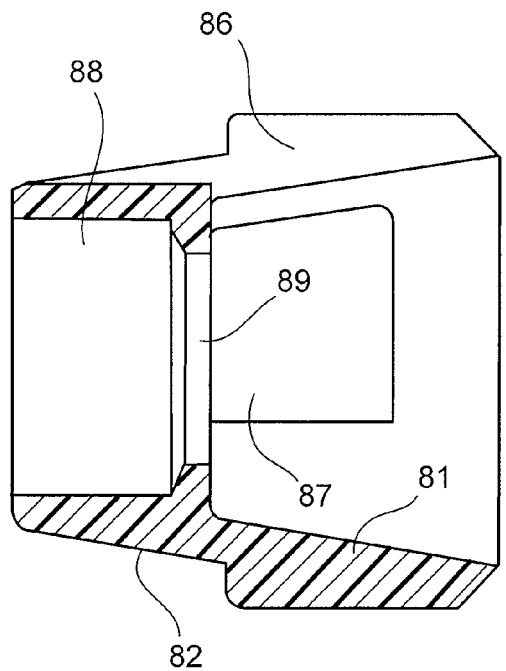
FIG. 7B is a cross-sectional view of the cervical cup of FIG. 7A, taken along line 7B-7B.

Referring to FIGS. 7A and 7B, the cervical cup 80 includes the annular body 81, a cup base 82 at a proximal end 83a and a rim 84 at a distal end 83b. The rim 84 is beveled to permit an anatomical landmark and incision backstop during use. The cervical cup 80 is formed of a material suitable for medical devices, that is, a medical grade material. Plastics, such as polyvinylchloride, polycarbonate, polyolefins, polypropylene, polyethylene or other suitable medical grade plastic, or metals, such as stainless steel or aluminum, can be used. The annular body 81 presents an outer peripheral, generally cylindrical surface 85 which extends between the rim 84 and the cup base 82. A laterally-extending slot 86 is positioned on the cylindrical surface 85 to permit use of surgical instruments. Viewing windows 87 may be disposed in and extend through the outer cylindrical surface 85.

The cup base 82 defines a socket 88 for captively receiving the uterine manipulating tip base 52. The cup base 82 also includes an aperture 89 extending between the socket 88 and the annular body 81 for receiving the uterine manipulating tip 53 (FIG. 4A) when cervical cup 80 is mounted on the uterine manipulator 20. When cervical cup 80 is mounted on the uterine manipulator 20, the uterine manipulating tip 53 extends axially through annular body 81, as shown in FIG. 1. Suitable cervical cups are commercially available from Cooper Surgical, Trumbull, Conn., under the KOH Cups™ and KOH Cup™ marks, such as Cooper Surgical item numbers KCP-30-2, KCP-35-2, KCP-40-2, KCS-30, KCS-35, and KCS-40.

Figure 8:
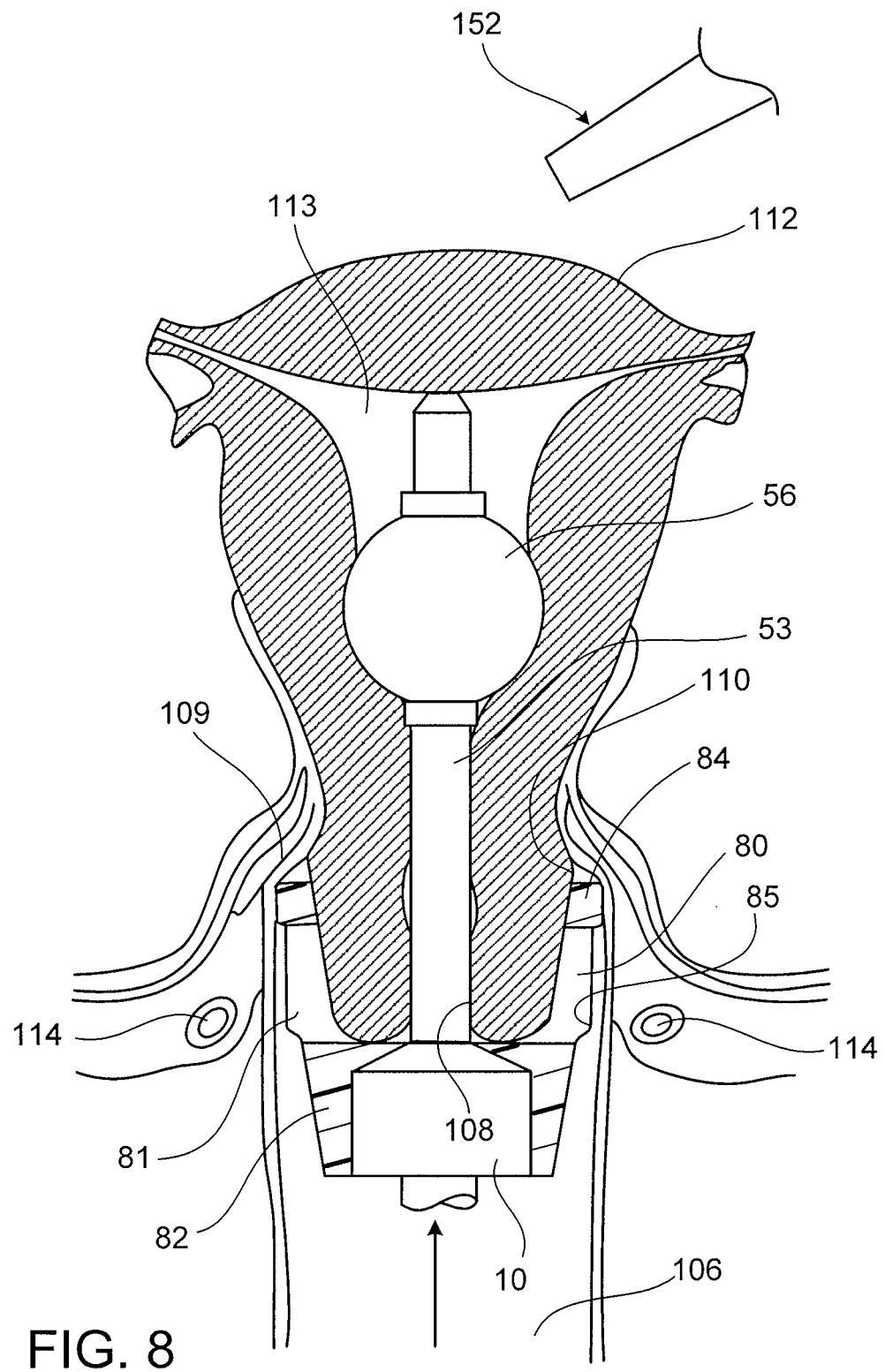
FIG. 8 is an anterior, cross-section view of a uterus showing a fully inserted uterine manipulator assembly.
Figure 9:
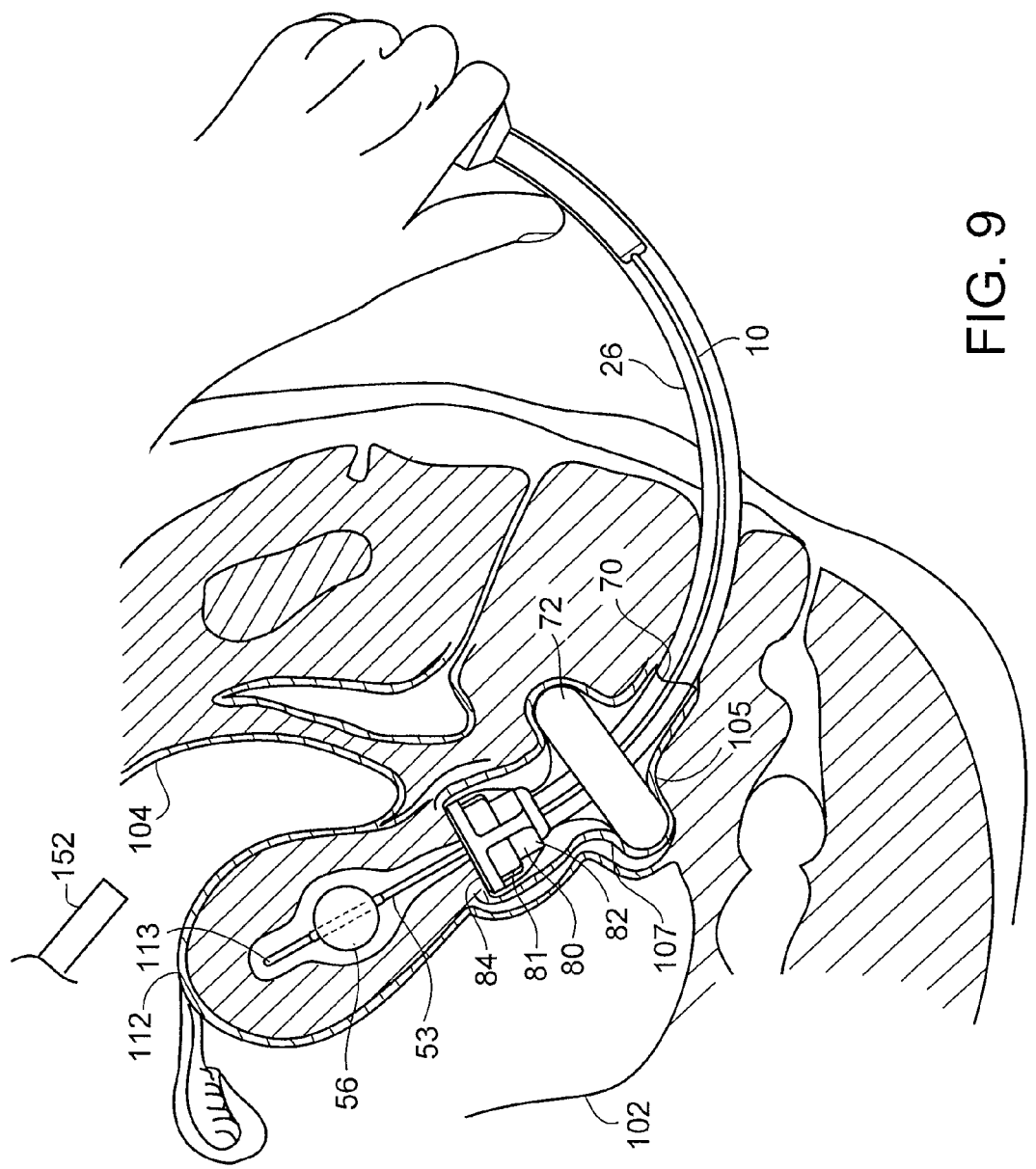
FIG. 9 is a cross-sectional side view of a pelvic cavity showing a uterine manipulator assembly holding a uterus in an anteverted position.

The uterine manipulator assembly 10 may be used in number of procedures which require manipulation of the uterus including surgical procedures such as hysterectomies. In one example, the uterine manipulator assembly 10 is used in a total laparoscopic hysterectomy (TLH) surgery. A patient is prepared for TLH surgery according to known procedures. Once prepared, the patient's abdominal cavity 102 is inflated with a gas (e.g., $CO_2$) to facilitate accessibility to and visibility of the female pelvic organs. Surgical instruments including a laparoscope 152, are inserted through the abdomen wall 104 into the abdominal cavity 102, as shown in FIGS. 8 and 9.

Next, the uterine manipulator assembly 10 is inserted into the vaginal cavity 106. When inserted, the cervix 108 is received into the annular body 81 of the cervical cup 80 and the rim 84 is placed into engaging relationship with the apex 109 of the formix 110. In this position, the cervical cup 80 provides an anatomical landmark at the base of the uterus 112 (i.e., where the cut needs to be) and also help to inhibit unintended damage to the ureters 114 by pushing them out of the way. The uterine manipulating tip 53 is fully inserted into the uterus 112 and the balloon 56 is inflated to come into engaging relationship with the uterus interior surface 113. Once the uterine manipulator assembly 10 is inserted into the vaginal cavity 106, the vaginal occluder 70 may be inflated (e.g., with sterile, water-based fluid) to seal the distal vaginal cavity 107 from the proximal vaginal cavity 105. The vaginal occluder 70 inhibits, e.g., prevents, the escape of gas used to inflate the abdominal cavity 102 during and following the first of any colpotomy incisions.

A surgeon or physician can then manipulate or move the uterus 112 into a desired position to perform surgery (e.g., to cut around the base of the uterus). After the uterus 112 is completely incised such that the uterus 112 is totally free in the abdominal cavity 102 and held only by the uterine manipulator assembly 10, the vaginal occluder 70 is deflated and the uterine manipulator assembly 10 is removed through the vagina.

Other Embodiments

While certain embodiments have been described above, other embodiments are possible.

Figure 10A:
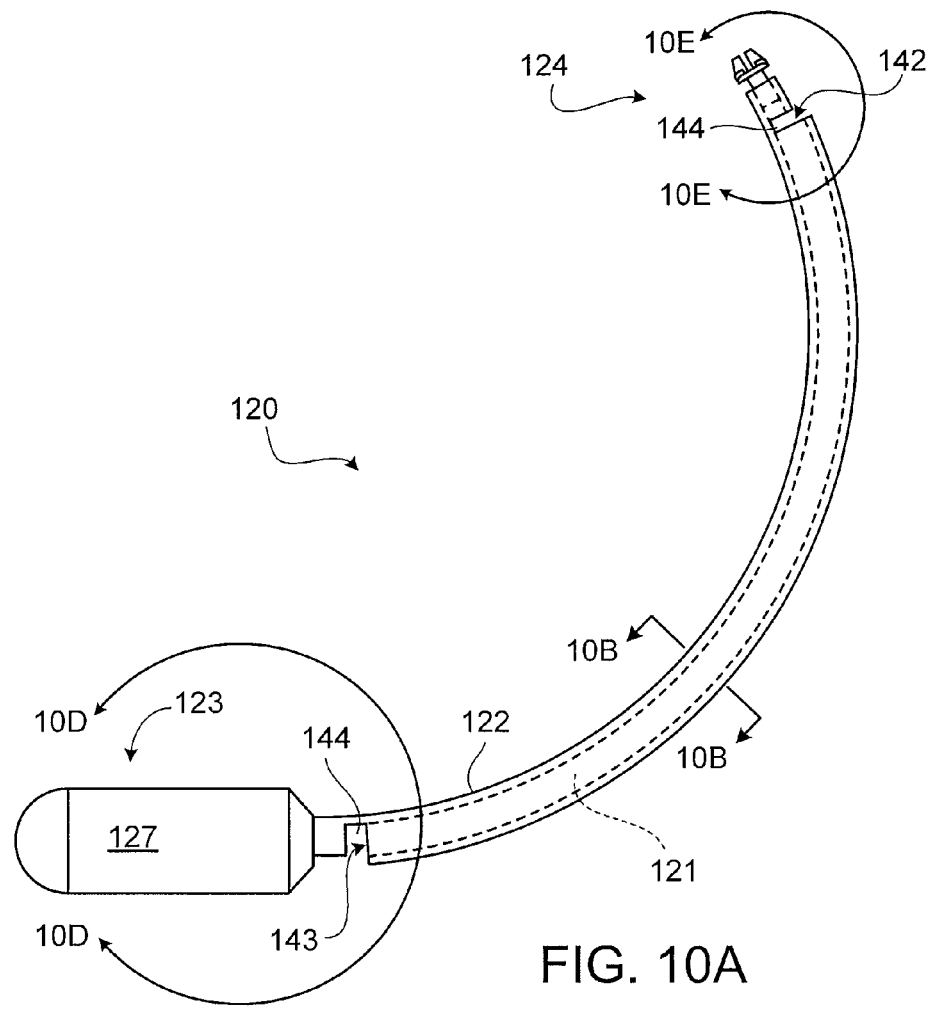
FIG. 10A is a side view of an embodiment of a uterine manipulator having a centrally located C-shaped channel for receiving and retaining catheter tubes.
Figure 10B:
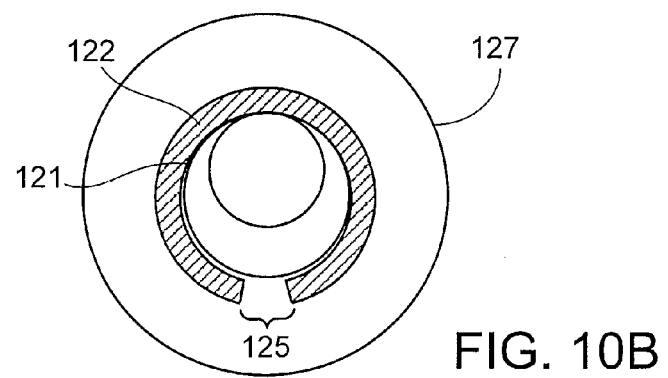
FIG. 10B is a cross-sectional view of the uterine manipulator of FIG. 10A, taken along line 10B-10B.
Figure 11A:
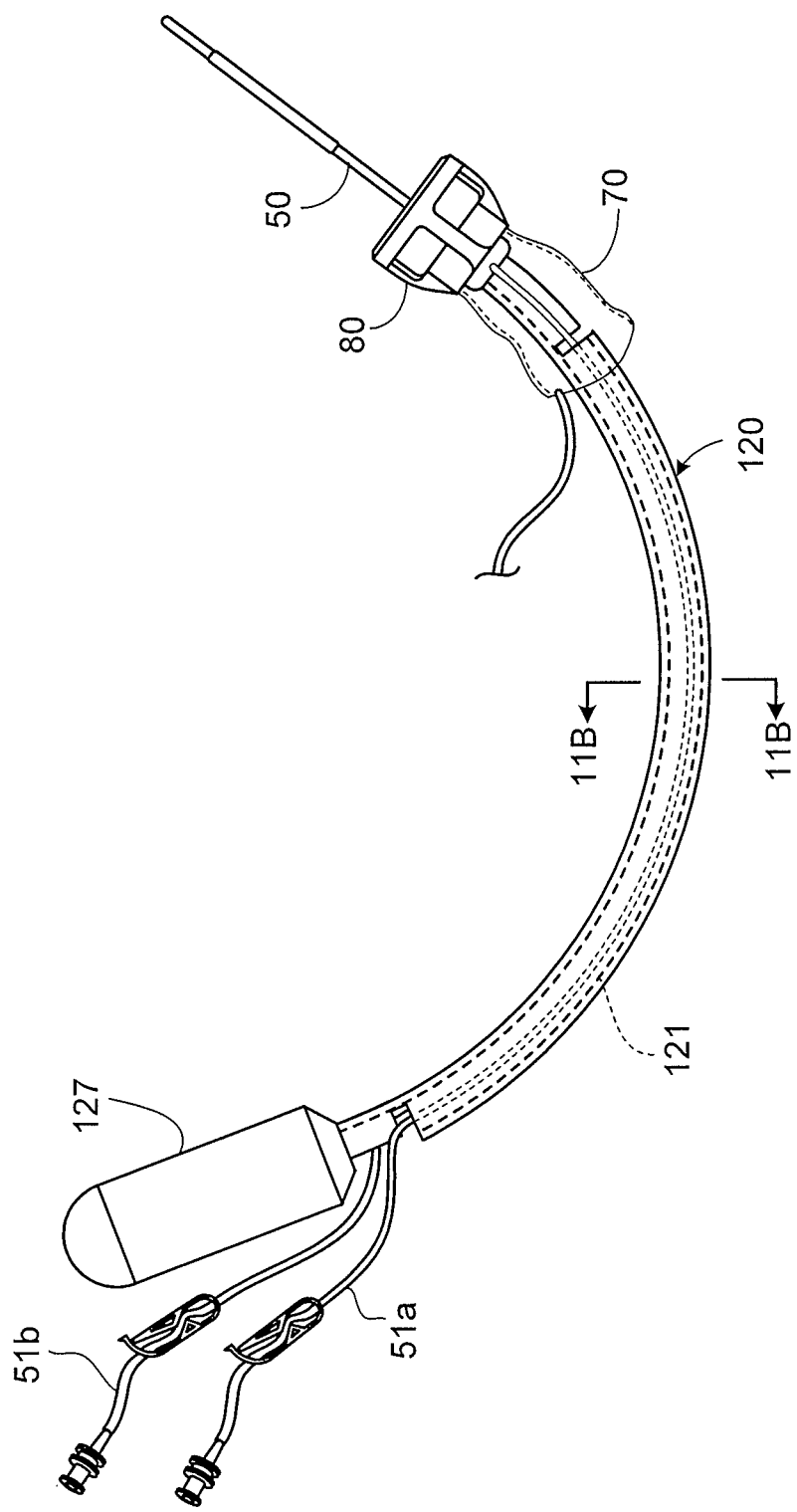
FIG. 11A is a side view of a uterine manipulator assembly with the uterine manipulator of FIG. 10A.
Figure 11B:
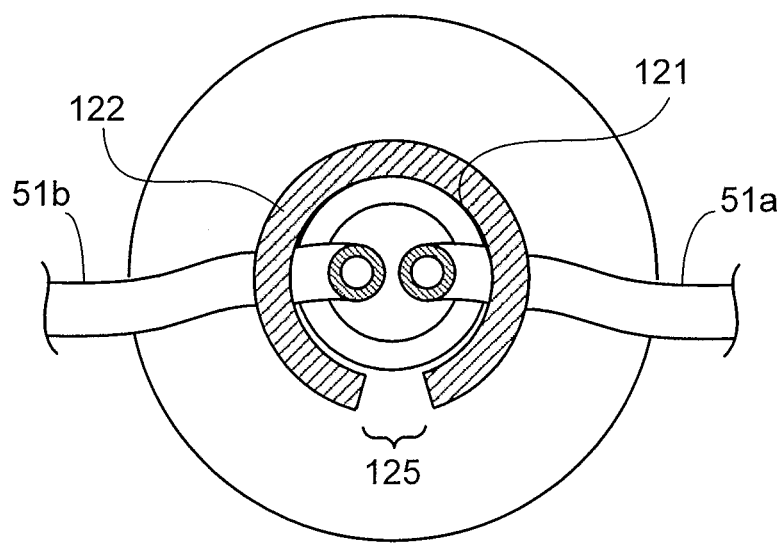
FIG. 11B is a cress-sectional view of the uterine manipulator assembly of FIG. 11A, taken along lines 11B-11B.

As an example, although embodiments of a uterine manipulator have been described above in which channels for receiving and retaining catheter tubing are spaced radially about a substantially solid shaft, in some embodiments, as illustrated in FIGS. 10A-10E, 11A and 11B, a uterine manipulator 120 can include a substantially hollow, arcuate shaft 122 that includes a centrally located C-shaped channel 121 capable of receiving and retaining a plurality of catheter tubes 51a, 51b (FIGS. 11A and 11B). The shaft 122 has a proximal end portion 123 and a distal end portion 124. The channel 121 extends between a first open end 142 at the distal end portion 124 and a second open end 143 at the proximal end portion 123 of the shaft. As shown in FIG. 10B, the shaft 122 also includes an opening 125 that extends along the length of the channel 121 and is substantially parallel thereto. The opening 125 allows the catheter tubes 51a, 51b (FIGS. 11A and 11B) to be inserted into and removed from the channel 121. In some cases, the width w of the opening is the same size as the diameter of the catheter tubers 51a, 51b. The second open end 143 allows the ends of catheter tuber 51a, 51b, which may include luer fittings 68 (FIG. 11A), to extend outwardly from the channel 121 at the proximal end portion 123 of the shaft 122. The shaft 122 may also include lateral slots 144 adjacent the first and/or second open ends 142, 143 to help ease insertion of the catheter tubes 51a, 51b into the channel 121. Friction between the catheter tubes 51a, 51b and the shaft 122 and interaction between the tubes 51a, 51b help to keep the catheter tubes 51a, 51b retained within the channel 121.

A handle 127 is coupled to the proximal end portion 123 of the shaft 122. The handle 127 can be integrally formed with shaft 122 or a separate piece. As shown, for example, in FIGS. 10C and 10D, the handle 127 that is mounted on the proximal end portion 123 of the shaft 122. In this regard, the handle 127 includes an aperture 129 which receives the proximal end portion 123. The handle 127 is slid over the shaft 122 such that the proximal end portion 123 extends into the aperture 129. Referring still to FIGS. 10C and 10D, the handle 127 is held in place, relative to shaft 122, by a set-pin 130 which includes a press-fit connection with a first through-hole 131a in the handle 127 and second through-hole 131b in the shaft 122. Alternatively or additionally, the handle 127 can be fixed to the shaft 122 with adhesive and/or threaded fastener(s) and/or the aperture 129 can be sized to provide a press-fit connection with the shaft 122.

Referring to FIG. 10E, the uterine manipulator 120 also includes a tip hub 134 disposed at the distal end portion 124. The tip hub 134 is configured to releasably receive and support the tip mount 50 (FIGS. 4A and 4B). The tip hub 134 includes a pair of spaced apart flats 135 which extend upwardly from a first surface 136 of a base 137. A stem 138 extends from a second surface 139, opposite the first surface 136 of the base 137. A through hole 140 extends from the first surface 136 of the base 137 through the stem 138 and is sized to receive the rod 61 (FIG. 4A) of the tip mount 50. The stem 138 is received in an opening 141 in the shaft 122 in a press-fit manner, thereby securing the tip hub 134 to the shaft 122.

The various components of the uterine manipulator 120 including the shaft 122, the handle 127 and the tip hub 134 can be formed, e.g., molded and/or machined, from materials that are biocompatible and capable of withstanding medical device sterilization procedures such as by heat-based methods (e.g., steam autoclave or dry heat oven) so that the uterine manipulator 120 as a whole is reusable. Suitable materials that are capable of withstanding medical device sterilization procedures include metals, such as stainless steel and aluminum, and polymers, such as Polyoxymethylene (POM).

Figure 12A:
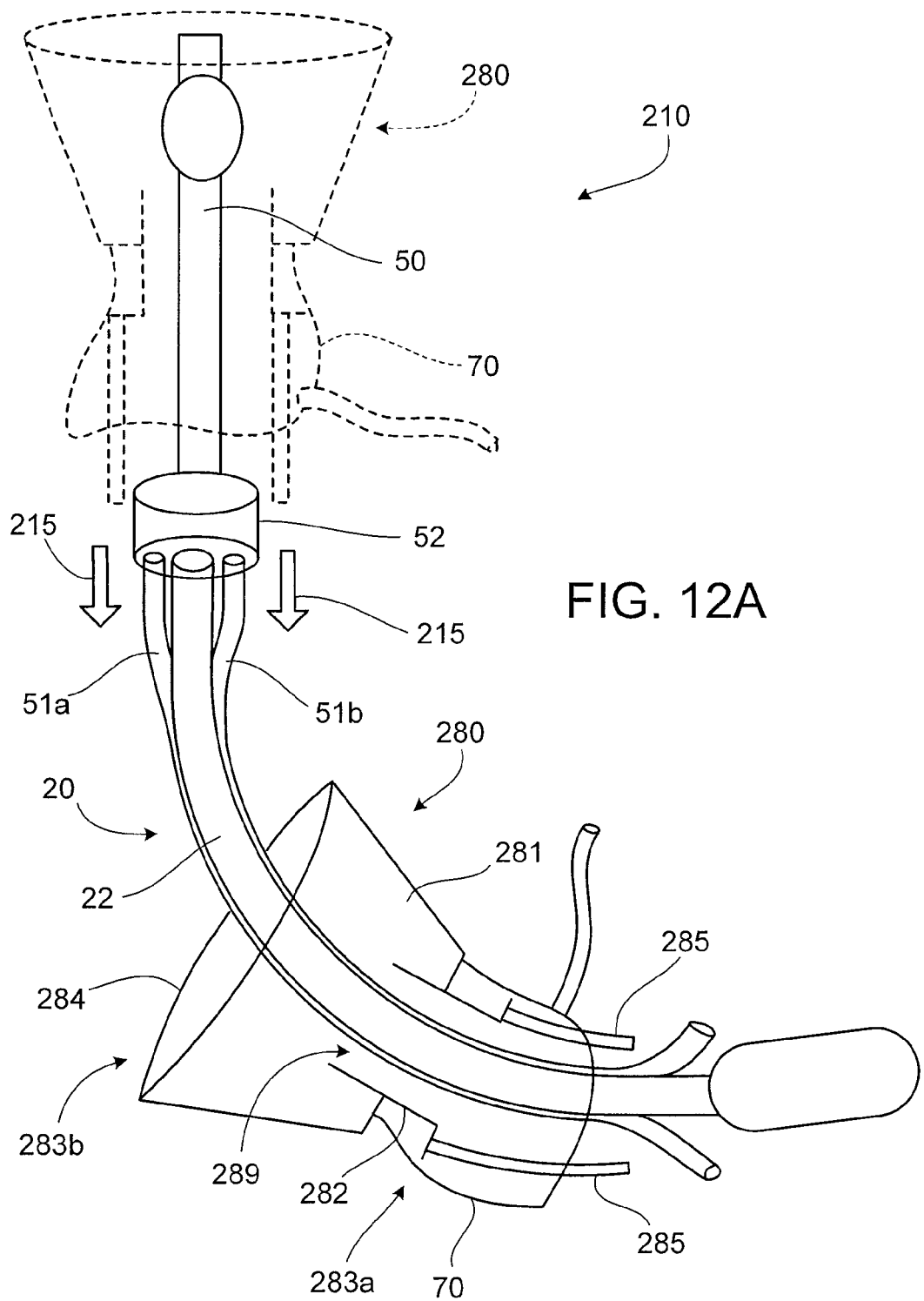
FIGS. 12A and 12B are schematic views of an embodiment of a uterine manipulator assembly with a displaceable cervical cup.
Figure 12B:
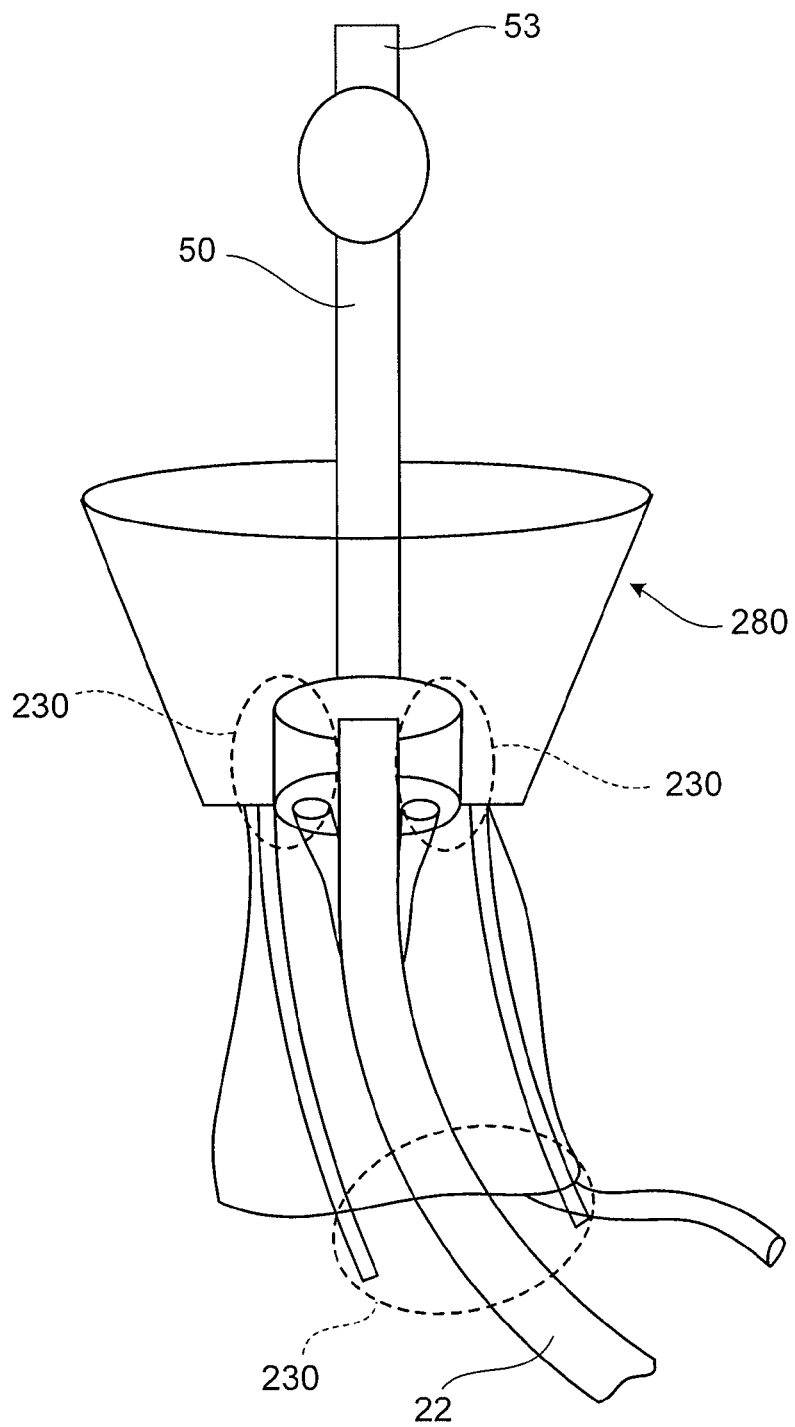

In some embodiments, the cervical cup can be configured to slide along the shaft. For example, FIGS. 12A and 12B illustrate an embodiment of a uterine manipulator assembly 210 that includes the uterine manipulator 20, the tip mount 50, the occluder 70, and a cervical cup 280 that is displaceable along the shaft 22 of the uterine manipulator 20. The cervical cup 280 includes an annular body 281 configured to receive a patient's cervix, a cup base 282 at a proximal end 283a and a rim 284 at a distal end 283b. The rim 284 can be beveled to permit an anatomical landmark and incision backstop during use. The cup base 282 includes an aperture 289 which is sized to fit over the manipulating tip base 52 and the shaft 22 of the uterine manipulator 20. The cervical cup 280 also includes cup extensions 285 which extend outwardly from the cup base 282. As illustrated in FIG. 12A, the cervical cup 280 can be placed over the tip mount 50 and slid proximally down (arrows 215) the shaft 22 of the uterine manipulator 20 prior to use. The cervical cup 280, which can have the occluder 70 attached via an adhesive, mechanical assembly, or injection molding, is moved down the shaft 22 of the uterine manipulator 20 to such a location that visualization of the cervix and the cervical os is not substantially limited by the cup 280 during insertion of the uterine manipulator assembly 210 into a patient. Once the uterine manipulator assembly 210 is placed inside the vagina and the tip 53 has been placed through the cervical os, the cup 280 is subsequently moved distally over the uterine manipulator shaft 22 to mate with the manipulating tip base 52. The channels 21 permit the cup 280 to be advanced over the shaft 22 with little or no interference with the catheter tubes 51a, 51b. A locking feature 230 (e.g., clamp, latch etc.) on the cup 230 and/or the shaft 22 allows for a positive stop and reference point so the cup 280 is placed in the correct position. For example, the locking feature 230 may be mounted to or part of the cup extensions 285 and configured to engage the shaft 22 and/or mounted to or part of the shaft 22 and configured to engage the cup extensions 285.

Figure 13A:
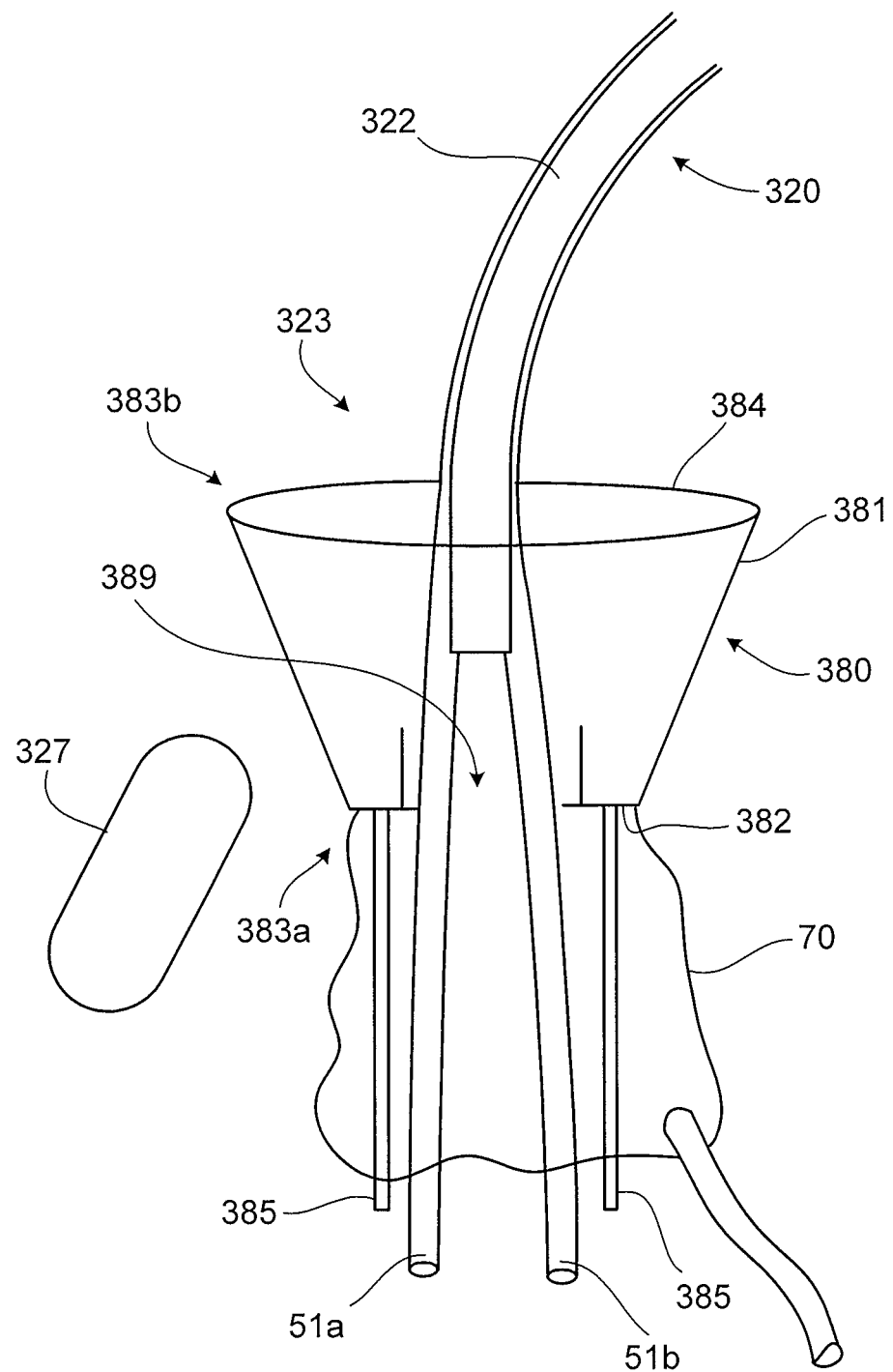
FIGS. 13A-13C are schematic views of another embodiment of a uterine manipulator assembly with a displaceable cervical cup.
Figure 13B:
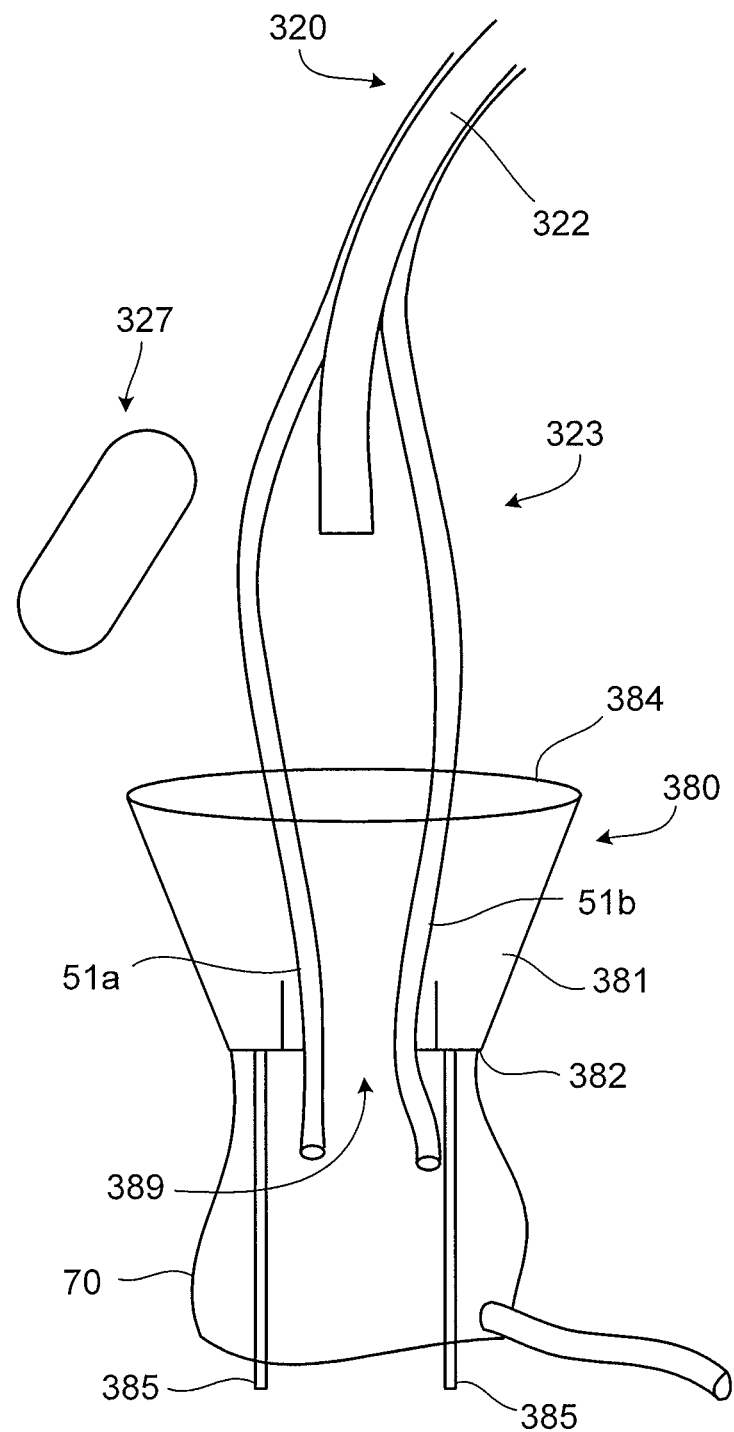
Figure 13C:
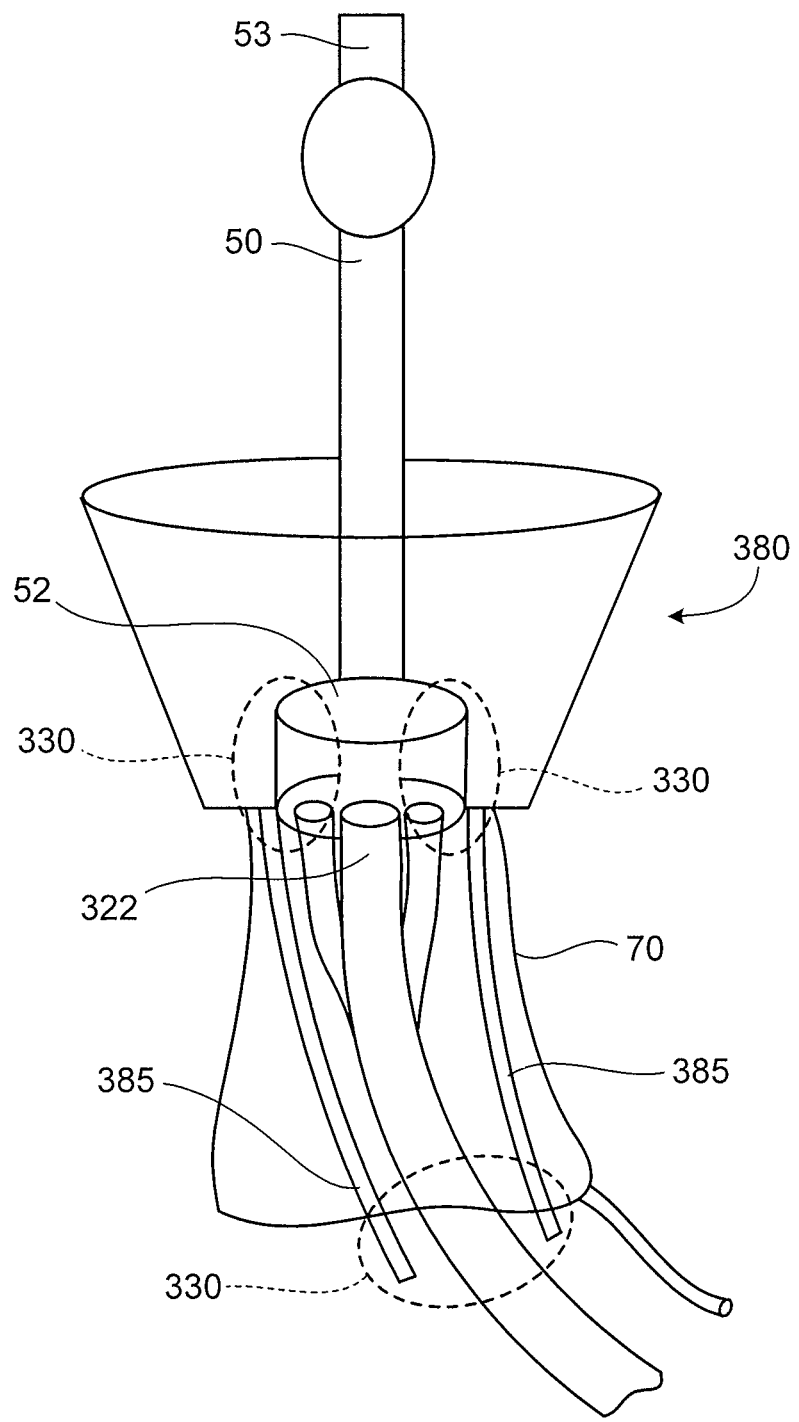

FIGS. 13A-13C illustrate another embodiment of a uterine manipulator assembly 310 that includes a uterine manipulator 320 with a removable handle 327, the tip mount 50, the vaginal occluder 70, and a cervical cup 380 that is slidably displaceable over a shaft 322 of the manipulator 320. The cervical cup 380 includes an annular body 381 configured to receive a patient's cervix, a cup base 382 at a proximal end 383a and a rim 384 at a distal end 383b. The rim 384 can be beveled to permit an anatomical landmark and incision backstop during use. The cup base 382 includes an aperture 389 which is sized to fit slidably over the shaft 322, as shown in FIGS. 13A and 13B. The cervical cup 380 also includes cup extensions 385 which extend outwardly from the cup base 282. The handle 327 may have a threaded connection with a proximal end portion 323 of the shaft 322 allowing the handle 327 to be removed from the shaft 322. Referring to FIGS. 13A and 13B, with the handle 327 removed from the shaft 322 and the catheter tubes 51a, 51b of the tip mount 50 passed through the aperture 389 of the cervical cup 380, the cup 380 is advanced over the proximal end portion 323 of the shaft 322. The handle 327 is then placed back on the proximal end portion 323 of the shaft 322. The cup 380 is maintained in a position at or near the proximal end portion 323 of the shaft 322 during insertion of the uterine manipulator assembly 310 into a patient such that visualization of the patient's cervix and the cervical os is not substantially limited by the cup 380. Once the assembly 310 is placed inside the patient's vagina and the tip 53 has been placed through the cervical os, the cup 380 is subsequently moved distally over the uterine manipulator shaft 322 to mate with the manipulating tip base 52. For example, the aperture 389 can be sized to provide a press-fit connection with the manipulating tip base 52 and/or the cup 380 may include a locking feature 330, such as a clamp or a latch, that is configured to engage the manipulating tip base 52. Alternatively or additionally, the locking feature 330 can be mounted to or part of the cup extensions 385 and configured to engage the shaft 322 and/or mounted to or part of the shaft 322 and configured to engage the cup extensions 385.

Figure 14A:
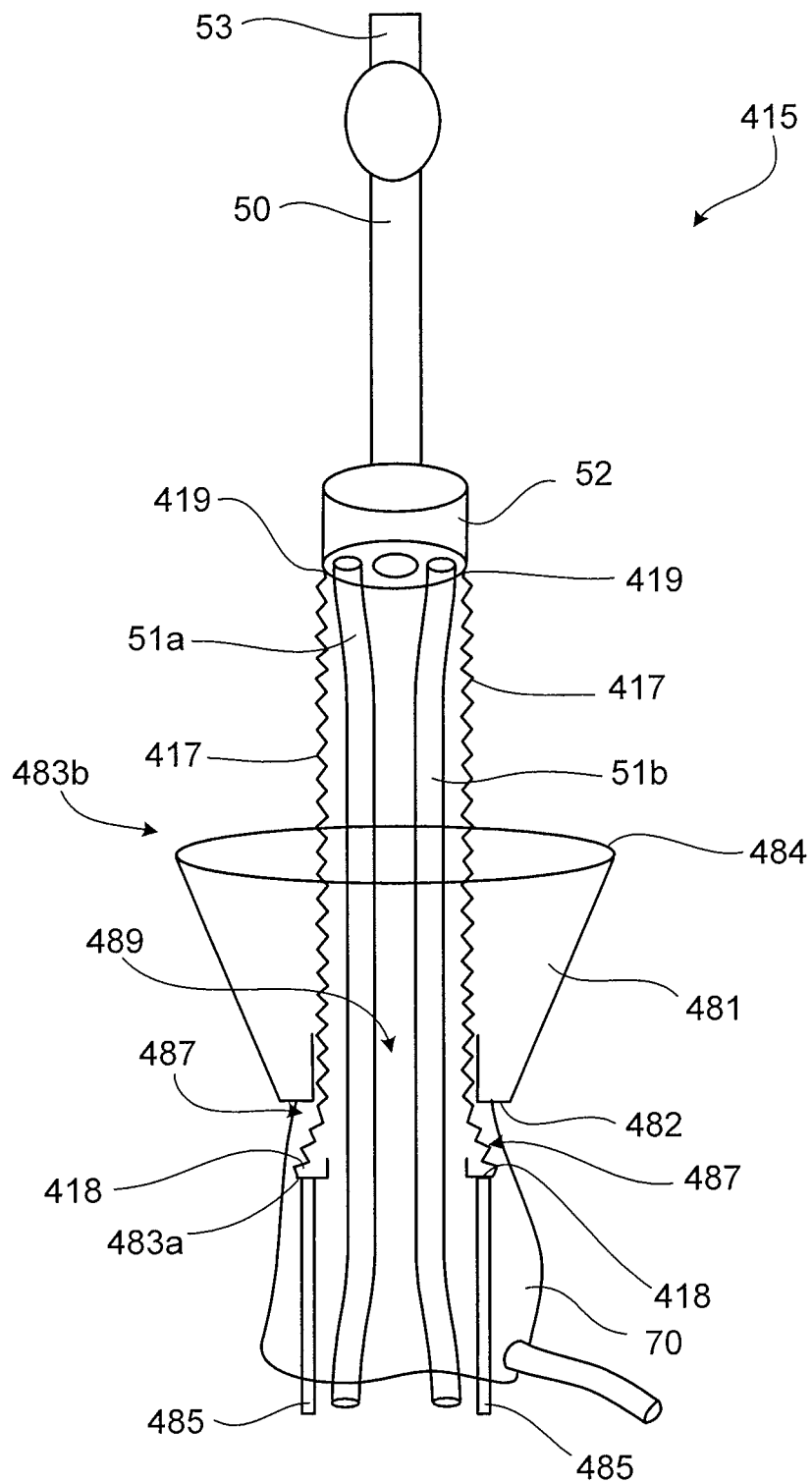
FIG. 14A is a schematic view of an integrated tip assembly.
Figure 14B:
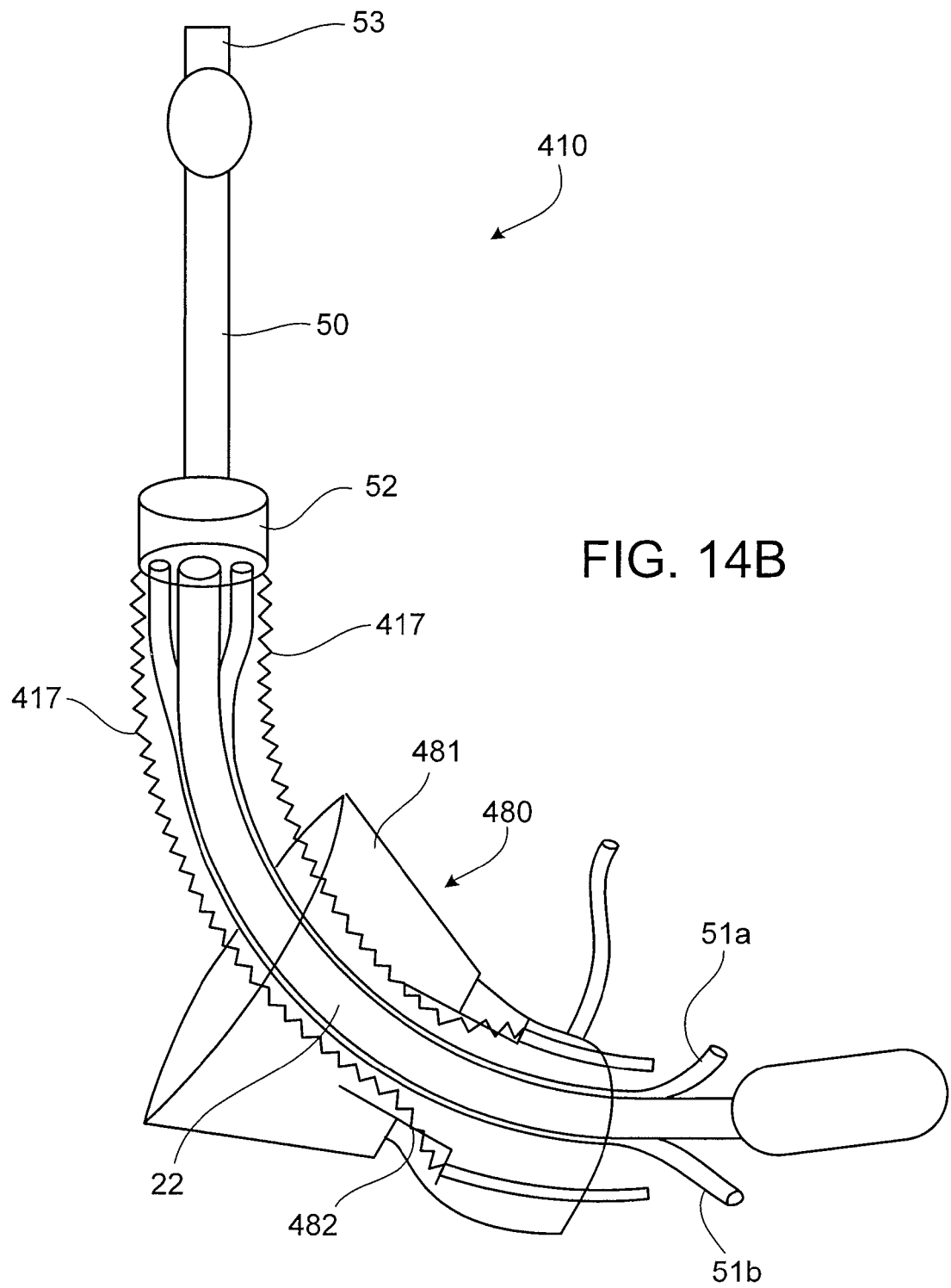
FIGS. 14B and 14C are schematic views of a uterine manipulator assembly with the integrated tip assembly of FIG. 14A.
Figure 14C:
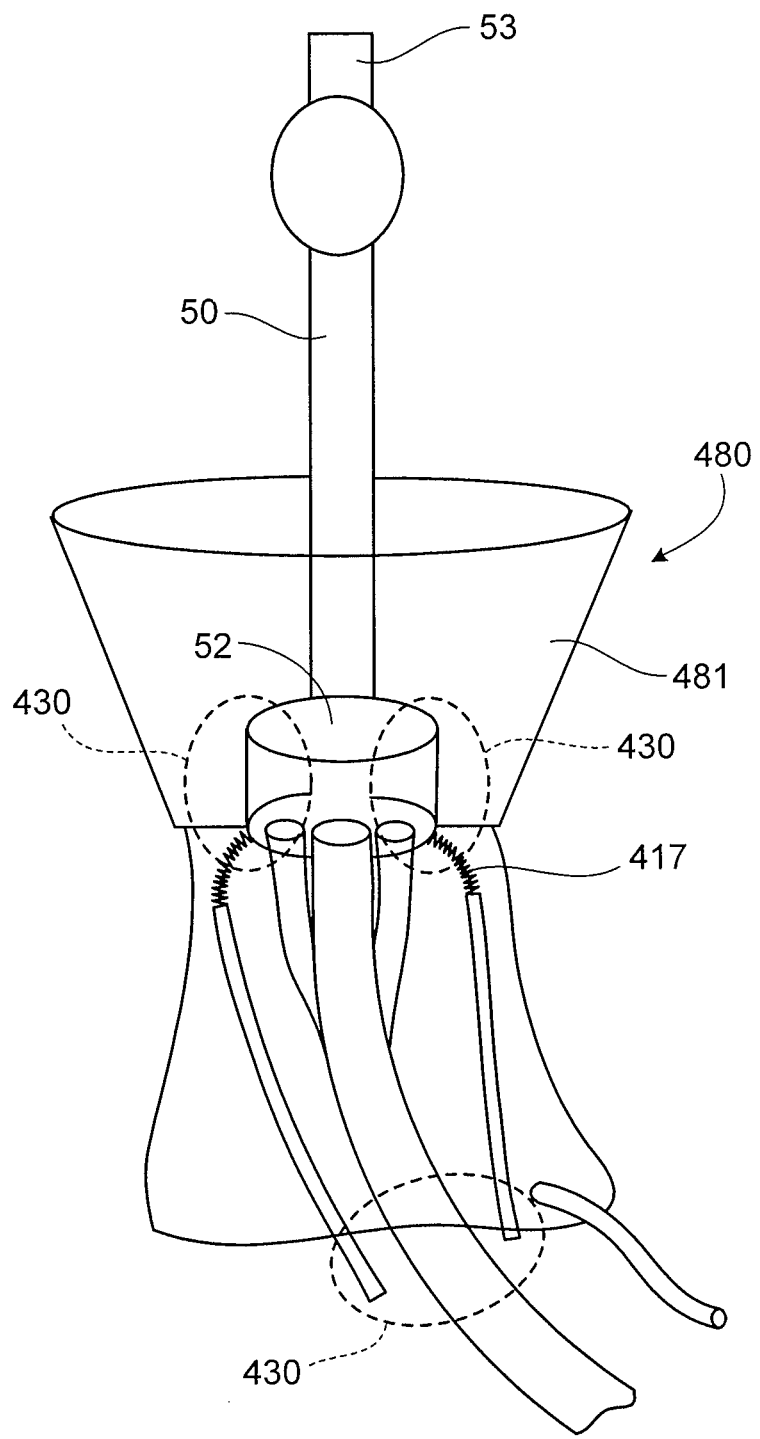

Referring to FIGS. 14A-14C, in another embodiment a uterine manipulator assembly 410 includes the uterine manipulator 20 and an integrated tip assembly 415 that includes the tip mount 50, a cervical cup 480, and the vaginal occluder 70, which is attached to the cervical cup 480 via an adhesive, mechanical assembly, or injection molding. The cervical cup 480 includes an annular body 481 configured to receive a patient's cervix, a cup base 482 at a proximal end 483a and a rim 484 at a distal end 483b. The rim 484 can be beveled to permit an anatomical landmark and incision backstop during use. The cup base 482 includes an aperture 489 which is sized to fit slidably over the shaft 22 of the uterine manipulator 20. The cervical cup 380 also includes cup extensions 385 which extend outwardly from the cup base 382. The integral tip assembly 415 includes a pair of collapsible connecting members 417. The connecting members 417 may be strips of pleated material formed from, for example, medical grade silicon. The connecting members 417 each have a proximal end 418 and a distal end 419. The distal ends 419 of the connecting members are attached to the manipulating tip base 52, e.g., via an adhesive. The proximal ends 418 of the connecting members 417 extend through the aperture 489 in the cup 480 and then through openings 487 in the cup base 482 and are attached to the primal end 483a of the cup 480, e.g., via an adhesive.

During assembly, the occluder 70 and the cervical cup 480 are advanced over the distal end portion 24 of the shaft 22 and the manipulating tip base 52 is brought into contact with the tip hub 34 (FIG. 3E) of the shaft 22. For example, the aperture 489 can be sized to provide a press-fit connection with the manipulating tip base 52 and/or the cup 480 may include a locking feature 430, such as a clamp or a latch, that is configured to engage the manipulating tip base 52. Alternatively or additionally, the locking feature 430 can be mounted to or part of the cup extensions 485 and configured to engage the shaft 22 and/or mounted to or part of the shaft 22 and configured to engage the cup extensions 485.

The cup 480 and occluder 70 portion of the assembly 415 is pushed towards the proximal end portion 23 of the shaft 22, extending the connecting members 417. The uterine manipulator assembly 410 is then placed, tip first, inside the patient. Once the assembly 410 is placed inside the vagina and the tip 53 has been placed through the cervical os, the cup 480 is subsequently moved distally over the uterine manipulator shaft 22 to mate, e.g., in a press-fit manner, with the manipulating tip base 52, as illustrated in FIG. 14C. As the cervical cup 480 is advanced along the shaft 22, the connecting members 417 collapse around the cup base 482.

Other embodiments are within the scope of the following claims.

What is claimed is:

1. A uterine manipulator assembly comprising:
    a tip mount comprising:
        a tip base and a tip that extends from a surface of the tip base, the tip base having a larger diameter than the tip such that the tip base abuts a cervix of a patient when the tip of the tip mount is extended into a uterine cavity of the, and
        one or more catheter tubes in fluid communication with the tip;
    an elongate shaft having a proximal end and a distal end, the distal end of the elongate shaft being configured to be inserted into a vagina, and the distal end of the elongate shaft being configured to matingly engage the tip mount such that the tip mount can be releasably secured to the elongate shaft, and
    a cup comprising a cup body and an elongate extension connected to the cup body, the cup having a first open end configured to receive a cervix, the cup being configured to be mounted on the elongate shaft in a manner such that the cup is slidable along the elongate shaft, the extension comprising a locking feature that locks the cup in a locked position along the elongate shaft, the cup matingly receiving the tip base when the tip mount is coupled to the elongate shaft and the cup is in the locked position,
    wherein the elongate shaft forms one or more channels extending between the distal and proximal ends, the one or more channels being formed by one or more respective recessed regions that extend radially inward from an outer surface of the shaft, the one or more respective recessed regions being open along the outer surface of the shaft and being configured to releasably receive the one or more catheter tubes of the tip mount such that the one or more catheter tubes can be releasably retained within the one or more channels.

2. The uterine manipulator assembly of claim 1, further comprising a tip hub disposed at the distal end of the elongate shaft, the tip hub being configured to releasably receive and support the tip mount.

3. The uterine manipulator assembly of claim 1, wherein the cup is configured to be coupled to the elongate shaft via the tip mount.

4. The uterine manipulator assembly of claim 1, wherein the cup is configured to be coupled to the elongate shaft such that the cup is slidable between the proximal and distal ends of the elongate shaft.

5. The uterine manipulator assembly of claim 1, further comprising a vaginal occluder attached to the cup, wherein the vaginal occluder is operable to inhibit the passage of fluid through a vaginal cavity.

6. The uterine manipulator assembly of claim 1, wherein the cup is connected to the tip mount by one or more collapsible connecting members.

7. The uterine manipulator assembly of claim 1, wherein the tip comprises an expandable member and at least one of the one or more catheter tubes is in fluid communication with the expandable member.

8. The uterine manipulator assembly of claim 1, further comprising a vaginal occluder configured to be coupled to the cup, wherein the vaginal occluder is operable to inhibit the passage of fluid through a vaginal cavity.

9. The uterine manipulator assembly of claim 1, wherein the elongate shaft is substantially arcuate.

10. The uterine manipulator assembly of claim 2, wherein the tip hub is configured to align the one or more catheter tubes of the tip mount in a predetermined position relative to the elongate shaft such that the one or more catheter tubes of the tip mount are substantially aligned with the one more channels.

11. The uterine manipulator assembly of claim 1, wherein the elongate shaft comprises a mounting interface.

12. The uterine manipulator assembly of claim 11, wherein the mounting interface comprises one or more flat regions on the elongate shaft.

13. The uterine manipulator assembly of claim 1, further comprising a handle disposed at the proximal end of the elongate shaft.

14. The uterine manipulator assembly of claim 1, wherein the elongate shaft comprises a plurality of said channels.

15. The uterine manipulator assembly of claim 14, wherein the plurality of said channels are spaced radially from a central axis of the elongate shaft.

16. The uterine manipulator assembly of claim 15, wherein the tip mount comprises a plurality of said catheter tubes, and each of the channels is configured to receive and support a single one of the catheter tubes of the tip mount.

17. The uterine manipulator assembly of claim 16, wherein each of the channels is configured to retain one of the catheter tubes in a position substantially flush with the outer surface of the elongate shaft.

18. The uterine manipulator assembly of claim 1, wherein the elongate shaft further comprises one or more openings extending along the channels, the one or more openings being configured to allow catheter tubing to be inserted into and removed from the channels.

19. The uterine manipulator assembly of claim 1, wherein the elongate shaft is formed of a material or materials capable of withstanding medical device sterilization procedures.

20. The uterine manipulator assembly of claim 1, wherein the elongate shaft is reusable, and the tip mount is constructed for one-time use.

21. A uterine manipulator assembly comprising:
    a tip mount comprising a tip base and a tip that extends from a surface of the tip base, the tip base having a larger diameter than the tip;
    a cup configured to matingly receive the tip base;
    an elongate shaft having a proximal end and a distal end, the distal end being configured to be inserted into a vagina; and
    a tip hub disposed at the distal end and configured to releasably receive and support the tip mount such that the tip mount can be releasably coupled to the elongate shaft, wherein the elongate shaft forms one or more channels extending between the distal and proximal ends, the one or more channels being formed by one or more respective recessed regions that extend radially inward from an outer surface of the shaft, the one or more respective recessed regions being open along the outer surface of the shaft and being configured to releasably receive catheter tubing such that one or more catheter tubes extending from the tip mount can be releasably retained within the one or more channels when the tip mount is coupled to the tip hub, and wherein the elongate shaft comprises a locking feature to lock the cup in a locked position along the elongate shaft when the cup is slid distally along the elongate shaft toward the distal end of the elongate shaft, and the locking feature is arranged so that the cup matingly engages the tip base of the tip mount when the tip mount is coupled to the elongate shaft and the cup is in the locked position.

22. The uterine manipulator assembly of claim 21, wherein the elongate shaft is substantially arcuate.

23. The uterine manipulator assembly of claim 21, wherein the tip hub is configured to align the tip mount in a predetermined position relative to the one or more channels of the elongate shaft.

24. The uterine manipulator assembly of claim 21, wherein the elongate shaft comprises a mounting interface.

25. The uterine manipulator assembly of claim 21, wherein the mounting interface comprises one or more flat regions on the elongate shaft.

26. The uterine manipulator assembly of claim 21, further comprising a handle disposed at the proximal end of the elongate shaft.

27. The uterine manipulator assembly of claim 21, wherein the elongate shaft comprises a plurality of said channels.

28. The uterine manipulator assembly of claim 27, wherein the channels are spaced radially from a central axis of the elongate shaft.

29. The uterine manipulator assembly of claim 28, wherein each of the channels is configured to receive and support a single catheter tube.

30. The uterine manipulator assembly of claim 29, wherein each of the channels is configured to retain a catheter tube in a position substantially flush with the outer surface of the elongate shaft.

31. The uterine manipulator assembly of claim 21, wherein the elongate shaft further comprises one or more openings extending along the channels, the one or more openings being configured to allow catheter tubing to be inserted into and removed from the channels.

32. The uterine manipulator assembly of claim 21, wherein the elongate shaft is formed of a material or materials capable of withstanding medical device sterilization procedures.

* * * * *

UNITED STATES PATENT AND TRADEMARK OFFICE
CERTIFICATE OF CORRECTION

PATENT NO. : 8,545,513 B2  
APPLICATION NO. : 12/565367  
DATED : October 1, 2013  
INVENTOR(S) : Kerry Blair et al.

Page 1 of 1

It is certified that error appears in the above-identified patent and that said Letters Patent is hereby corrected as shown below:

In the Claims

Column 11  
Claim 1, line 28, delete "the," and insert -- the patient, --  
Claim 1, line 30, delete "tip;" and insert -- tip; and --

Column 14  
Claim 27, line 1, delete "claim 21," and insert -- claim 24, and --

Signed and Sealed this  
Third Day of December, 2013

Margaret A. Focarino  
*Commissioner for Patents of the United States Patent and Trademark Office*

UNITED STATES PATENT AND TRADEMARK OFFICE
CERTIFICATE OF CORRECTION

PATENT NO.         : 8,545,513 B2                                                 Page 1 of 1
APPLICATION NO.    : 12/565367
DATED              : October 1, 2013
INVENTOR(S)        : Kerry Blair et al.

It is certified that error appears in the above-identified patent and that said Letters Patent is hereby corrected as shown below:

In the Claims

<u>Column 14,</u>
Claim 27, line 7, "claim 24" (as inserted in the Certificate of Correction issued December 3, 2013) is deleted and dependency of claim 27 is returned to its original state as it appears in printed patent --claim 21--.

<u>Column 14,</u>
Claim 25, line 1, delete "claim 21" and insert --claim 24--.

Signed and Sealed this
Twenty-second Day of July, 2014

Michelle K. Lee
*Deputy Director of the United States Patent and Trademark Office*